(12) United States Patent
Hara et al.

(10) Patent No.: US 10,209,177 B2
(45) Date of Patent: Feb. 19, 2019

(54) SIGNAL PROCESSING APPARATUS FOR ELIMINATING OBJECT REFLECTION NOISE IN OPTICAL TOMOGRAPHIC MEASUREMENT

(71) Applicant: Sony Corporation, Tokyo (JP)

(72) Inventors: Masaaki Hara, Tokyo (JP); Yoshiki Okamoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/559,916

(22) PCT Filed: Feb. 5, 2016

(86) PCT No.: PCT/JP2016/000613
§ 371 (c)(1),
(2) Date: Sep. 20, 2017

(87) PCT Pub. No.: WO2016/157680
PCT Pub. Date: Oct. 6, 2016

(65) Prior Publication Data
US 2018/0073978 A1 Mar. 15, 2018

(30) Foreign Application Priority Data
Mar. 31, 2015 (JP) .................................. 2015-070971

(51) Int. Cl.
*G01N 21/17* (2006.01)
*G01B 9/02* (2006.01)
(Continued)

(52) U.S. Cl.
CPC ......... *G01N 21/17* (2013.01); *G01B 9/02059* (2013.01); *G01B 9/02083* (2013.01);
(Continued)

(58) Field of Classification Search
CPC .. G01B 9/02025; G01B 9/0209; G01N 21/17; G01N 2021/1787; G01N 2021/516
See application file for complete search history.

(56) References Cited

U.S. PATENT DOCUMENTS 6,392,756 B1 * 5/2002 Li ..................... G01B 11/0641
356/369

FOREIGN PATENT DOCUMENTS

JP 2001-289781 A 10/2001
JP 2012-002598 A 1/2012
(Continued)

OTHER PUBLICATIONS

International Search Report and Written Opinion of PCT Application No. PCT/JP2016/000613, dated Apr. 26, 2016, 06 pages of ISRWO.

*Primary Examiner* — Hwa Lee
(74) *Attorney, Agent, or Firm* — Chip Law Group

(57) ABSTRACT

[Solving Means] A signal processing apparatus is a signal processing apparatus for an optical tomographic measurement apparatus that generates measurement light and reference light and measures a tomographic structure of a measurement object on the basis of a signal intensity of interference light between the reference light and return light of the measurement light from the measurement object. An arithmetic unit is configured to calculate a signal intensity of simple reflection among the return light of the measurement light, the simple reflection being one time of reflection at a plurality of layers virtually set in a depth direction from a surface layer side of the measurement object. The arithmetic unit is configured to calculate a signal intensity of multiple reflection on the basis of the signal intensity of the simple reflection, the signal intensity of multiple reflection being a
(Continued)

signal intensity of return light generated by being reflected at the plurality of layers three or more times.

7 Claims, 20 Drawing Sheets

(51) Int. Cl.
*G01N 21/45* (2006.01)
*G01N 21/47* (2006.01)
G01N 21/51 (2006.01)
G01B 11/06 (2006.01)

(52) U.S. Cl.
CPC ......... *G01B 9/02091* (2013.01); *G01N 21/45* (2013.01); *G01N 21/4795* (2013.01); *G01B 11/0675* (2013.01); *G01N 2021/1787* (2013.01); *G01N 2021/516* (2013.01); *G01N 2201/12* (2013.01)

(56) References Cited

FOREIGN PATENT DOCUMENTS

| | | |
|---|---|---|
| JP | 2012-2598 A | 1/2012 |
| JP | 5611259 B2 | 10/2014 |
| WO | 2011/158849 A1 | 12/2011 |

* cited by examiner

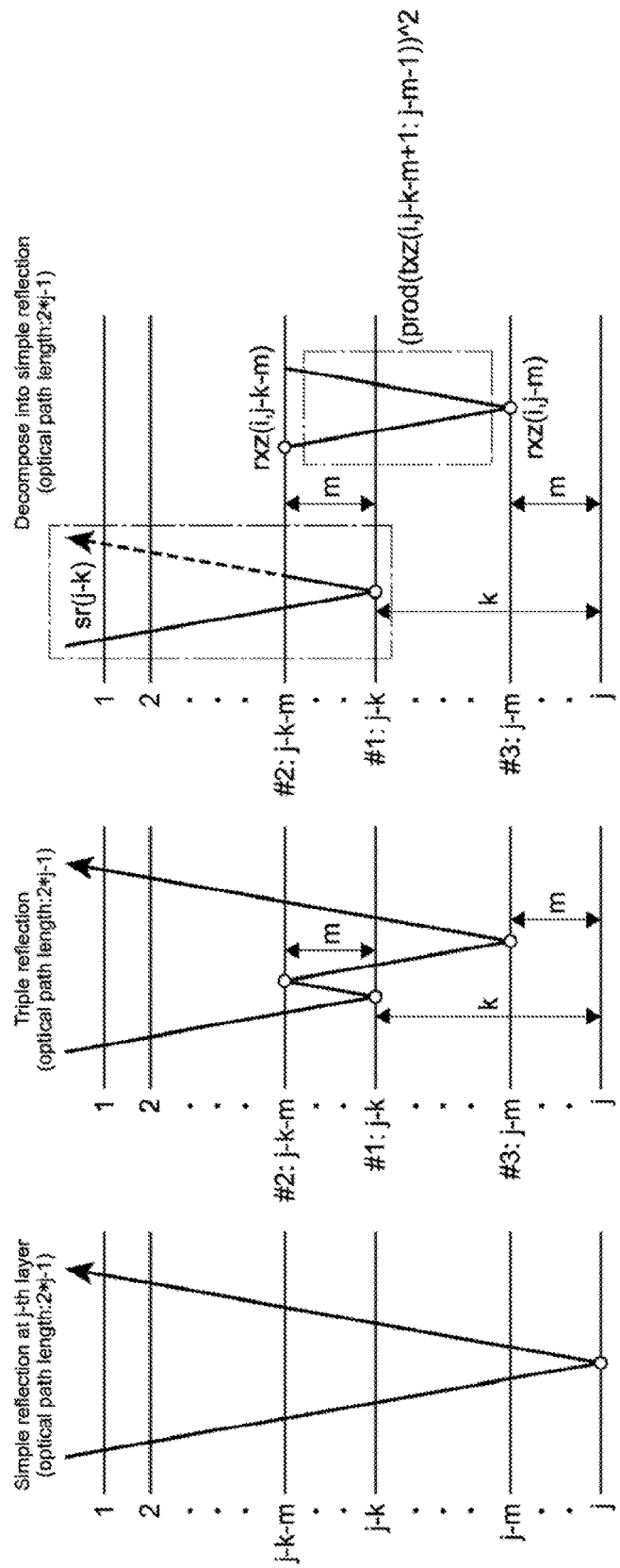

SIGNAL PROCESSING APPARATUS FOR ELIMINATING OBJECT REFLECTION NOISE IN OPTICAL TOMOGRAPHIC MEASUREMENT

CROSS REFERENCE TO RELATED APPLICATIONS

This application is a U.S. National Phase of International Patent Application No. PCT/JP2016/000613 filed on Feb. 5, 2016, which claims priority benefit of Japanese Patent Application No. JP 2015-070971 filed in the Japan Patent Office on Mar. 31, 2015. Each of the above-referenced applications is hereby incorporated herein by reference in its entirety.

TECHNICAL FIELD

The present technology relates to an optical tomographic measurement apparatus, a signal processing apparatus for processing a signal obtained thereby, and a signal processing method.

BACKGROUND ART

The OCT (Optical Coherence Tomography) technology is generally used in an apparatus for acquiring a tomographic image of an eyeball or the like. As an example of an apparatus using the OCT technology, for example, Patent Literature 1 discloses an optical tomographic imaging apparatus that removes coherent noise (artifact) generated by interference of a plurality of reflected light beams reflected by a plurality of layers. Specifically, interference occurs between highly reflective layers in a fundus, and coherence noise occurs in the image as an artifact at a position separated from the position where optical path lengths of measurement light and reference light in the tomographic image are equal to each other by a distance between the highly reflective layers. By blocking the reference light and using only the measurement light, coherent noise is detected (see paragraph 0034 of the specification and FIG. 3 of Patent Literature 1).

CITATION LIST

Patent Literature

Patent Literature 1: Japanese Patent No. 5611259

DISCLOSURE OF INVENTION

Technical Problem

In the optical tomographic measurement technology, in the case where the optical path length of return light from a point other than a measurement point in a measurement object matches with the optical path length of measurement light, the return light and the measurement light interfere with each other, which generates noise.

In view of the circumstances as described above, it is an object of the present technology to provide a signal processing apparatus, an optical tomographic measurement apparatus, and a signal processing method that effectively eliminate noise due to multiple reflection.

Solution to Problem

In order to achieve the above-mentioned object, a signal processing apparatus according to the present technology is a signal processing apparatus for an optical tomographic measurement apparatus that generates measurement light and reference light and measures a tomographic structure of a measurement object on the basis of a signal intensity of interference light between the reference light and return light of the measurement light from the measurement object.

An arithmetic unit is configured to calculate a signal intensity of simple reflection among the return light of the measurement light, the simple reflection being one time of reflection at a plurality of layers virtually set in a depth direction from a surface layer side of the measurement object. Further, the arithmetic unit is configured to calculate a signal intensity of multiple reflection on the basis of the signal intensity of the simple reflection, the signal intensity of multiple reflection being a signal intensity of return light generated by being reflected at the plurality of layers three or more times.

Since this signal processing apparatus calculates the signal intensity of multiple reflection as noise on the basis of the signal intensity of simple reflection, it is possible to perform processing of removing this on the basis of the signal intensity of the multiple reflection. Therefore, noise due to multiple reflection can be effectively removed.

The arithmetic unit may be configured to calculate respective signal intensities of the multiple reflection at the third and subsequent layers on the basis of pseudo simple reflection that occurs by decomposing a path of triple reflection occurring at the third and subsequent layers into a path of simple reflection, the surface layer being the first layer among the plurality of layers.

The arithmetic unit may be configured to subtract the respective signal intensities of the multiple reflection at the third and subsequent layers from the signal intensity of the simple reflection including the pseudo simple reflection.

Accordingly, noise is effectively removed from the signal intensity of interference light.

The arithmetic unit may be configured to calculate signal intensities of the simple reflection of the second and subsequent layers on the basis of reflectances of the second layer and subsequent layers and transmittances of the first layer and subsequent layers among the plurality of layers.

Accordingly, the arithmetic unit is capable of achieving a more realistic signal intensity of the simple reflection.

The arithmetic unit may be configured to set an absorptance to be constant in the plurality of layers and calculate the transmittance as a value obtained by subtracting the absorptance and the reflectance from 1.

An optical tomographic measurement apparatus includes: an optical system, a detector, and the above-mentioned arithmetic unit.

The optical system generates measurement light, reference light, and interference light between the reference light and return light of the measurement light from a measurement object.

The detector detects the interference light generated by the optical system.

A signal processing method according to the present technology is a signal processing method for generating measurement light and reference light and measuring a tomographic structure of a measurement object on the basis of a signal intensity of interference light between the reference light and return light of the measurement light from the measurement object.

The signal processing method includes calculating a signal intensity of simple reflection among the return light of the measurement light, the simple reflection being one time of reflection at a plurality of layers virtually set in a depth direction from a surface layer side of the measurement object.

Further, the signal processing method includes calculating a signal intensity of multiple reflection on the basis of the signal intensity of the simple reflection, the signal intensity of multiple reflection being a signal intensity of return light generated by being reflected at the plurality of layers three or more times.

Advantageous Effects of Invention

As described above, in accordance with the present technology, noise due to multiple reflection is effectively removed.

It should be noted that the effect described here is not necessarily limitative and may be any effect described in the present disclosure.

BRIEF DESCRIPTION OF DRAWINGS

FIGS. 9A, 9B and 9C are each a diagram for considering a method of specifically calculating a signal by triple reflection.

MODE(S) FOR CARRYING OUT THE INVENTION

1. Principle of OCT (Optical Coherence Tomography)

1) Basic Configuration of OCT

Figure 1A:
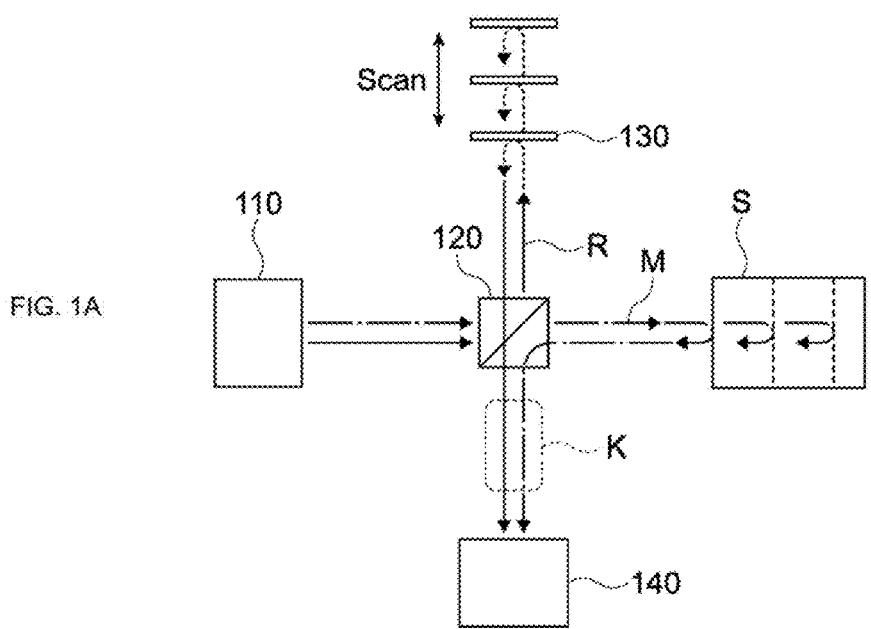
FIG. 1A shows a configuration of an optical tomograph for describing the detection principle of OCT.

FIG. 1A shows a configuration of an optical tomograph for describing the detection principle of OCT. Here, a TD (Time Domain) type optical tomograph is taken as an example. The optical tomograph (optical tomographic measurement apparatus) basically includes hardware of a Michelson interferometer.

Specifically, the optical tomograph includes a broadband light source 110, a beam splitter 120, a photodetector 140, and a reference mirror 130. The broadband light source 110 is a light source that generates broadband light (white light). The reference mirror 130 is configured to move in a plurality of stages in the light traveling direction (optical axis direction). Light from the broadband light source 110 is split by the beam splitter 120 into measurement light M and reference light R. The measurement light M is reflected by a measurement object S to generate return light, and the return light is reflected by the beam splitter 120 and enters the photodetector 140. The reference light R is reflected by the reference mirror 130, is transmitted through the beam splitter 120, and enters the photodetector 140.

Figure 1B:
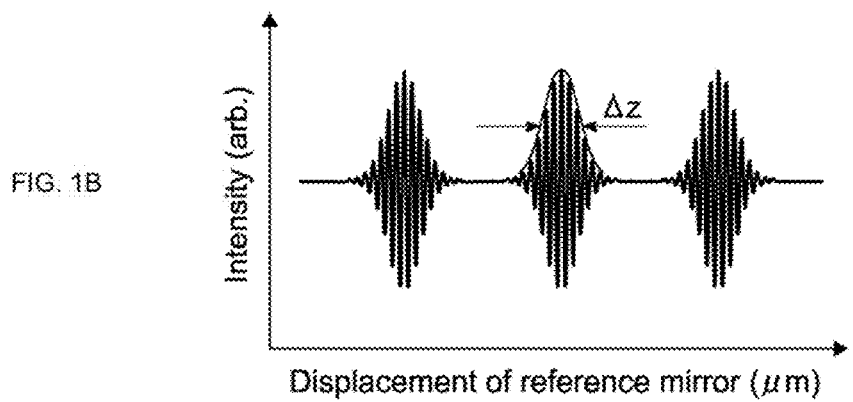
FIG. 1B shows a signal obtained by a photodetector using the TD (Time Domain) method in FIG. 1A.

When the optical path lengths of the return light and the reference light match, they interfere with each other, and interference light K thereof is detected by the photodetector 140. The signal obtained by the photodetector 140 is detected by heterodyne detection as shown in FIG. 1B, for example. Note that in FIG. 1B, three areas (areas detected as low frequencies) with high signal intensity of the return light in the depth direction of the measurement object indicated by the horizontal axis are detected.

As the position of the reference mirror 130 in the optical axis direction is changed in a stepwise manner, the optical path length of the reference light is also changed in a stepwise manner. As a result, the measurement point (measurable reflection position) where the optical path length of the measurement light matches is changed in a stepwise manner in the light traveling direction (depth direction) within the measurement object. That is, the optical tomograph is capable of observing the internal structure of the measurement object by detecting the intensity of return light generated for each of a plurality of layers virtually set in the depth direction of the measurement object.

Note that in the following description, the terms "observation" and "measurement" are used unified for "measurement". Further, in the following description, "intensity" means "signal intensity", and the term "reflection intensity" means "signal intensity of reflection".

The OCT method mainly includes an FD-SD (Fourier Domain Spectral Domain) method and an FD-SS (Fourier Domain Swept Source) method in addition to the above-mentioned TD method.

In the FD-SD method, although the same broadband light source as that in the TD method is used, the reference mirror is fixed, and interference light between the return light of the measurement light and the reference light is spectrally separated (wavelength separated) by a diffraction grating. Then, spectrally separated light is detected by the photodetector. Therefore, it is possible to improve the speed and the resolution.

The FD-SS method requires a special light source capable of wavelength sweeping at high speed, i.e., a special light source that generates coherent light having different wavelength bands at each instant. However, the FD-SS method is superior in speed, resolution, and observation depth.

Figure 1C:
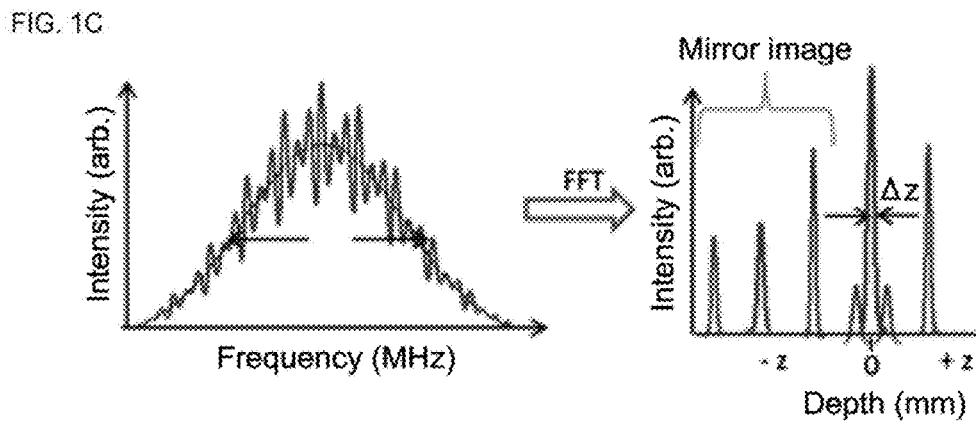
FIG. 1C shows a signal obtained by a photodetector using the FD (Fourier Domain) method and a signal obtained after performing FFT (Fast Fourier Transform) processing on the signal.

FIG. 1C shows a signal (left) obtained by the photodetector using the FD-SD and FD-SS methods and a signal (right) obtained after performing FFT (Fast Fourier Transform) processing on the signal.

2) Signal Detection Processing by OCT

Hereinafter, signal detection processing in the above-mentioned FD-SS system, i.e., processing on a signal detected by the photodetector will be described.

The signal desired as the output of the OCT is the reflection intensity of the measurement light in the measurement object. In the case where the depth direction of the measurement object is the x direction and its position is x, the depth distribution of the reflection intensity is f(x). Coherent light having an angular frequency $\omega=2\pi c/\lambda$ is divided by the beam splitter 120 into two light beams of reference light and light to be irradiated onto the measurement object. In the case where the intensity of the reference light is $E_r$ and the intensity of the return light from the measurement object is $E_s$, the light intensities thereof are represented by the following equations 1 and 2, in which $x_r$ represents the optical path length of the reference light, $x_s$ represents the optical path length of the measurement light, and c represents the light velocity ($3\times10^8$ [m/s]).

$$E_r = \frac{1}{\sqrt{2}} \exp(j\omega x_r/C) \quad [\text{Math. 1}]$$

$$E_s = \frac{1}{\sqrt{2}} \exp(j\omega x_s/C) \quad [\text{Math. 2}]$$

The intensity $I_{rs}$ when these two are added together and interfere with each other is represented by the following equation 3 as a function of $\omega$, $x_r$, and $x_s$.

$$\begin{aligned} I_{rs} &= |E_r + E_s|^2 \quad [\text{Math. 3}]\\ &= (E_r + E_s)\cdot(E_r^* + E_s^*)\\ &= \frac{1}{2}\left\{\exp\left(\frac{j\omega x_r}{c}\right) + \exp\left(\frac{j\omega x_s}{c}\right)\right\} \cdot\\ &\quad \left\{\exp\left(\frac{-j\omega x_r}{c}\right) + \exp\left(\frac{-j\omega x_s}{c}\right)\right\}\\ &= \frac{1}{2}\left\{1 + 1 + \exp\left(\frac{j\omega(x_r - x_s)}{c}\right) + \exp\left(\frac{-j\omega(x_r - x_s)}{c}\right)\right\} \end{aligned}$$

In the case where the optical path difference x is defined as $x=x_r-x_s$, the equation 3 can be replaced with an equation 4.

$$I_{rs} = 1 + \cos(\omega x/c) \quad [\text{Math. 4}]$$

In the case where the constant 1 is neglected and $t=x/c$ in the equation 4, the equation 4 becomes the following equation 5 in which $\omega=2\pi/T$.

$$Irs = \cos(\omega t) \quad [\text{Math. 5}]$$

When the equation 5 is Fourier transformed, an equation 6 is derived. This is the basic principle of the FD-SS OCT.

$$I_{rs} = \delta(t-nT) + \delta(t+nT) \quad [\text{Math. 6}]$$

In the case where measurement is performed discretely at the sampling frequency $f_s=1/T$, the kth angular frequency $\omega_k$ is represented by the following equation 7.

$$\omega_k = (\omega_s/N)\cdot k = (2\pi f_s/N)\cdot k = (2\pi/N/T)\cdot k \quad [\text{Math. 7}]$$

The n-th distance difference $x_n$ and the n-th time difference $t_n$ are linked by the following equation 8 with the light velocity c.

$$t_n = \frac{x_n}{c} = nT \quad [\text{Math. 8}]$$

An intensity F(k) obtained at a certain angular frequency is represented by the following equation 9.

$$F(k) = \sum_{m=0}^{N-1} f(m)\cos(\omega_k\cdot t_m) = \sum_{m=0}^{N-1} f(m)\cos(2\pi/N\cdot k\cdot m) \quad [\text{Math. 9}]$$

f(m) represents the reflection intensity from the m-th distance difference $x_m$.

An equation 10 is developed by performing inverse Fourier transform (IDFT) on the equation 9 in anticipation of obtaining f(m) from F(k).

$$\begin{aligned} &\left(\frac{1}{N}\right)\sum_{k=0}^{N-1} F(k)\cdot\exp\left(\frac{j2\pi}{N}\cdot n\cdot k\right) = \quad [\text{Math. 10}]\\ &\left(\frac{1}{2N}\right)\sum_{k=0}^{N-1}\sum_{m=0}^{N-1} f(m)\cdot\left\{\exp\left(\frac{j2\pi}{N}\cdot m\cdot k\right) + \exp\left(\frac{-j2\pi}{N}\cdot m\cdot k\right)\right\}\cdot\\ &\exp\left(\frac{j2\pi}{N}\cdot n\cdot k\right) = \left(\frac{1}{2N}\right)\sum_{k=0}^{N-1}\sum_{m=0}^{N-1} f(m)\cdot\\ &\left\{\exp\left(\frac{j2\pi}{N}\cdot(n+m)\cdot k\right) + \exp\left(\frac{j2\pi}{N}\cdot(n-m)\cdot k\right)\right\} \end{aligned}$$

Here, from an equation 11 in the equation 10, an equation 12 is derived by using the formula for the sum of a geometric progression.

$$\sum_{k=0}^{N-1} \exp\left(\frac{j2\pi}{N} \cdot (n+m) \cdot k\right) \qquad \text{[Math. 11]}$$

$$\frac{1 - \exp(j2\pi \cdot (n+m))}{1 - \exp\left(\frac{j2\pi}{N} \cdot (n+m)\right)} \qquad \text{[Math. 12]}$$

However, since the denominator is non-zero and the numerator is zero in the equation 12, the equation 12 becomes zero. Therefore, the following equations 13 and 14 are established.

$$\left(\frac{1}{2N}\right) \sum_{k=0}^{N-1} \sum_{m=0}^{N-1} f(m) \cdot \exp\left(\frac{j2\pi}{N} \cdot (n+m) \cdot k\right) = f(-n)/2 \qquad \text{[Math. 13]}$$

$$\left(\frac{1}{2N}\right) \sum_{k=0}^{N-1} \sum_{m=0}^{N-1} f(m) \cdot \exp\left(\frac{j2\pi}{N} \cdot (n-m) \cdot k\right) = f(n)/2 \qquad \text{[Math. 14]}$$

From the above, when IDFT is performed on F(k), the following equation 15 is obtained.

$$\{f(n) + f(-n)\}/2 \qquad \text{[Math. 15]}$$

Therefore, it is understood that only f(m) is extracted and f(x) only needs to be used as the depth distribution of the reflection intensity in the case where the depth direction is x.

From the basic principle of the derived FD-SS OCT, the following can be seen.

(a) When the coherent length of light of each wavelength is as long as possible, it is capable of interfering with the reflected light from the deep part with large optical path difference.

(b) Since the number of discrete wavelengths that can be measured by sweeping corresponds to the number of slices in the depth direction one to one, it is better that the number of usable wavelengths is larger.

Improvement in the resolution in the depth direction by using a light source with a shorter coherent length in the TD method and the fact of (a) above conflict with each other. However, the fact of (b) is important. The distribution of the reflectance of the measurement object is continuous and is not divided into layers. However, in the FD-SS OCT, the measurement positions in the depth direction are discrete rather than continuously distributed, and the number of measurable layers matches with the number of wavelengths.

2. Factors that can Cause Noise

Figure 2:
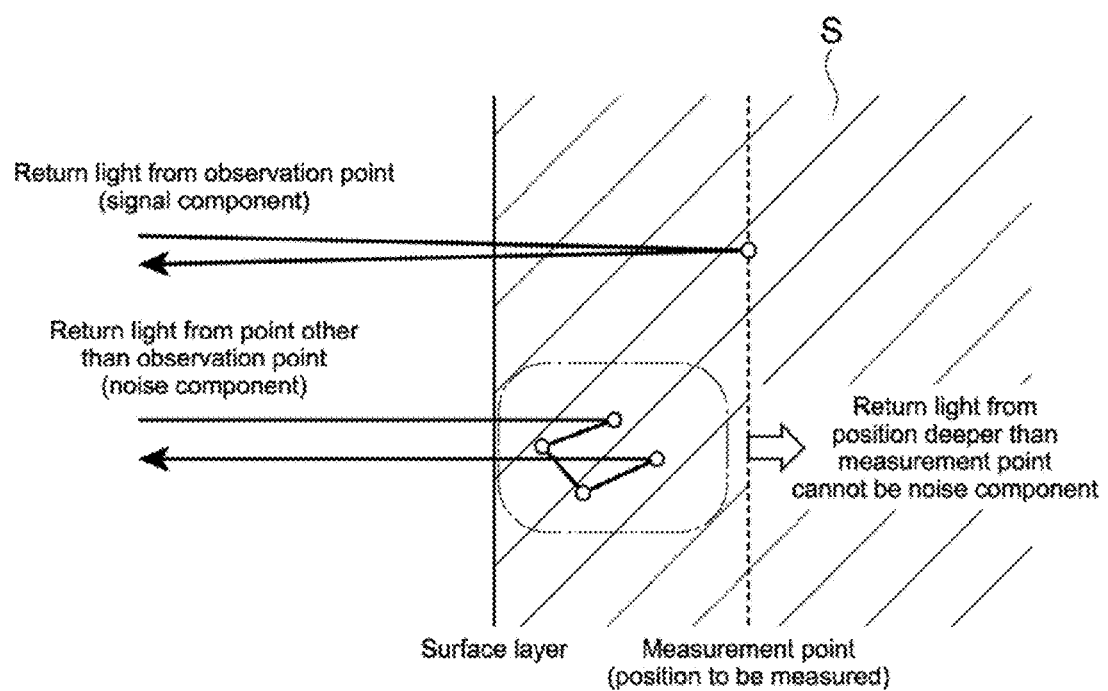
FIG. 2 is a diagram for describing the generation principle of noise of return light.

Next, the problem of OCT will be described. As shown in FIG. 2, in the OCT, return light from a point other than the measurement point also interferes as long as the optical path length thereof matches with the optical path length of the reference light, which causes noise and adversely affects the acquired image.

However, the return light from a point other than the measurement point has been scattered a plurality of times at a "shallower" point than the measurement point, and the return light from a "deeper" position than the measurement point cannot be a noise component. This is because the optical path lengths do not match. Therefore, in the case of measuring the surface of the measurement object, there is no above-mentioned noise component.

In actual biological tissues, scattering is dominant, and the OCT selectively detects only the "on-axis component of back scattering (component propagating in the vicinity of the optical axis among the light scattered by the biological tissues)." In order to describe the principle in an easy-to-understand manner, the inner area from the surface layer of the measurement object to a predetermined depth is considered as a virtual multilayer structure having a plurality of reflection surfaces, and the motion in each layer is referred to as "reflection" in this specification. That is, the "reflected light" is light reflected by an arbitrary layer inside the measurement object. Meanwhile, the "return light" in this specification means light that is reflected one or more times in the measurement object, emitted from the measurement object, and returned to the photodetector.

Figure 3:
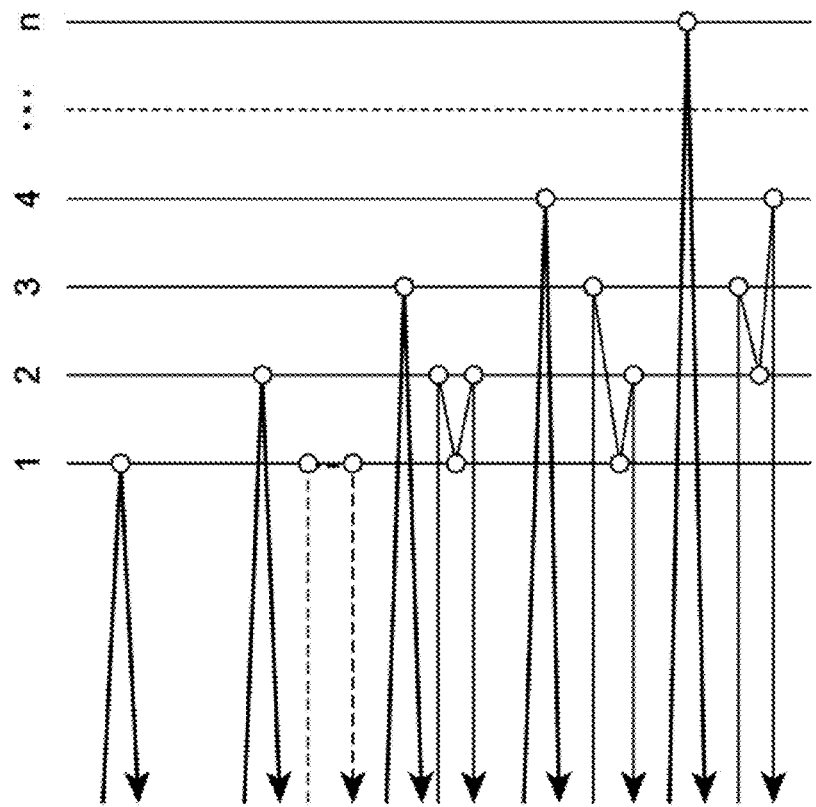
FIG. 3 shows the motion of return light in a multilayer structure.

FIG. 3 shows the motion of light in the multilayer structure. The actual biological tissues do not have such a multilayer structure. Since OCT performs measurement at discrete fixed intervals, assuming that the result is a representative value in the vicinity of the measurement point, it can be regarded as a multilayer structure as shown in the figure. Further, the "layer" actually represents the "depth position", but the term "layer" is used for the sake of description. Since the component outside the axis (optical axis) among the return light from a point other than the measurement point can be removed by confocalization (pinhole), considering only the component along the axis, the motion of light in the multilayer structure has the following properties.

The first layer (surface layer) is not affected by other layers

The second layer is not affected by other layers

The third layer is affected by the first and second layers

The fourth layer is affected by the first to third layers

The n-th layer (that is, n is a natural number) is affected by the 1st to n−1-th layers Note that in this FIG. 3, it is stipulated that the light generated as return light by three times of reflection is light mixed into the measurement light as noise.

From such consideration, it is theoretically possible to calculate all noise components by sequentially calculating the intensity of the noise component (multiple reflection to be described later) for each layer from the surface layer side to the deep layer side.

3. Simple Model of Tomographic Signal

Figure 4:
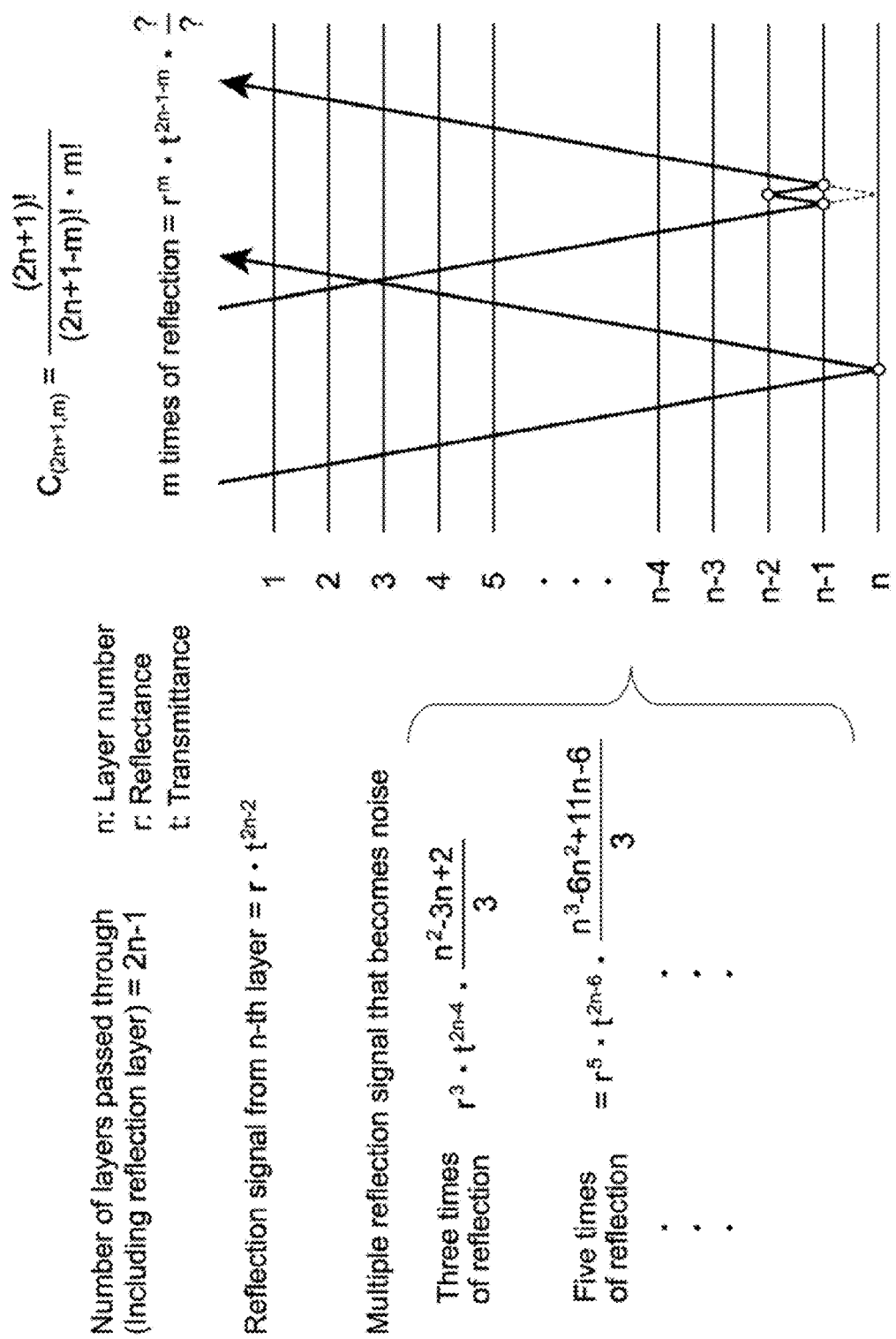
FIG. 4 shows a simple model of a tomographic signal.

FIG. 4 shows a simple model of a tomographic signal. Assumption is made that a reflectance r, a transmittance t, and an absorptance a of each layer are constant, and r+t+a=1. A signal that is subjected to simple reflection (reflection only once) from the n-th layer is proportional to the following equation 16.

$$r \cdot t^{2n-2} \qquad \text{[Math. 16]}$$

The intensity (power) of multiple reflection passed through the same number of layers 2n−1 can be represented as the following equation 17 in the case of m times of reflection. The multiple reflection mentioned here is three or more odd-numbered times of reflection, i.e., three or more times of reflection, which generates "return light".

$$r^m \cdot t^{2n-1-m} \qquad \text{[Math. 17]}$$

Since the magnitude of the noise is obtained by multiplying the equation 17 by the number of combinations of multiple reflection, it is represented by an equation 18 for three times of reflection and an equation 19 for five times of reflection.

$$r^3 \cdot t^{2n-4} \cdot \frac{n^2 - 3n + 2}{2} \quad \text{[Math. 18]}$$

$$r^5 \cdot t^{2n-6} \cdot \frac{n^8 - 6n^2 + 11n - 6}{3} \quad \text{[Math. 19]}$$

Note that in this specification, r is not "reflectance" in a strict sense. The reflectance of a component propagating in the specular direction of scattered light (i.e., the direction in which light returns in the depth direction) will be referred to as "reflectance" for the sake of convenience.

4. Combination of Optical Paths of Three Times of Reflection

In the case of considering the number of combinations of three times of reflection, the shortest path problem is considered. In the shortest path problem, the number of combinations of paths for arriving at the destination at a shortest distance 2n via three places from the departure point is considered. Then, the number of combinations can be calculated by the following equation 20. Note that the number of combinations of five or more times of multiple reflection can also be considered in terms of the shortest path problem similarly.

$$\sum_{k=1}^{n-2} k = \frac{n^2 - 3n + 2}{2} \quad \text{[Math. 20]}$$

Generally, since the reflectance r of the measurement object is smaller than 0.1 and r is raised to the fifth power in the case of five times of reflection and raised to the seventh power in the case of seven times of reflection in the OCT, the influence thereof is considered to be sufficiently small and negligible. In the following description, only three times of reflection will be described for simplicity. However, the scope of application of the present technology is not limited only to three times of reflection, and the present technology is applicable to five or more times of multiple reflection.

The present inventors have estimated, with respect to a signal obtained by the OCT, the influence of simple reflection which is an original signal and multiple reflection which becomes a noise component, by simulation using Matlab.

First, in the FD-SS OCT, since the depth is discretized and data is acquired, the characteristics of r, a, and t parameters are defined as follows. Here, the depth direction is represented by z, and the direction along one of two axes orthogonal to z is represented by x. In the following, only one of the two axes orthogonal to z is considered, and the axis is assumed to be the x direction for simplicity of description.

$$r = rz \text{ or } 0 \quad \text{(1) Reflectance:}$$

As described above, for example, rz<0.1. Further, assumption is made that r has three states of "constant value", "two kinds of 0 or rz", or "uniform random number of 0 to rz".

$$a = az \quad \text{(2) Absorptance:}$$

For example, az<0.1. Assumption is made that the absorptance a is constant, i.e., az.

$$t = 1 - az - rz \quad \text{(3) Transmittance:}$$

Assumption is made that the transmittance t is decreased by the amount corresponding to the reflectance and the absorptance.

In the case where the number of n divisions in the x direction is represented by nx and the number of n divisions in the depth direction is represented by nz, r, a, and t are all two-dimensional matrices of nx×nz. The return light returns only from the area of r(i,j)=rz(≠0) in which i is a sequence number in the x direction and j is a sequence number in the z direction.

The resolution of each area in the depth direction z is represented by dz, and the resolution in the direction x orthogonal to z is represented by dx. The resolution of a wavelength w of the light source used for measurement is represented by dw. Since the number of wavelengths and the number of divisions in the depth direction correspond to each other one to one, the number of wavelengths automatically becomes nz.

A reflection signal from a certain depth z(j) is transmitted through the regions from z(1) to z(j−1), reflected by z(j), transmitted through z(j−1) to z(1), and comes back. When this fact is written as it is with Matlab's description method, it becomes as follows.

$$\text{prod}(t(i,1:j-1))*r(i,j)*\text{prod}(t(i,1:j-1))$$

"prod" indicates the product of the array, and prod(t(i,1: j−1)) is (1)*t(2)* . . . *t(j−1).

Figure 5:
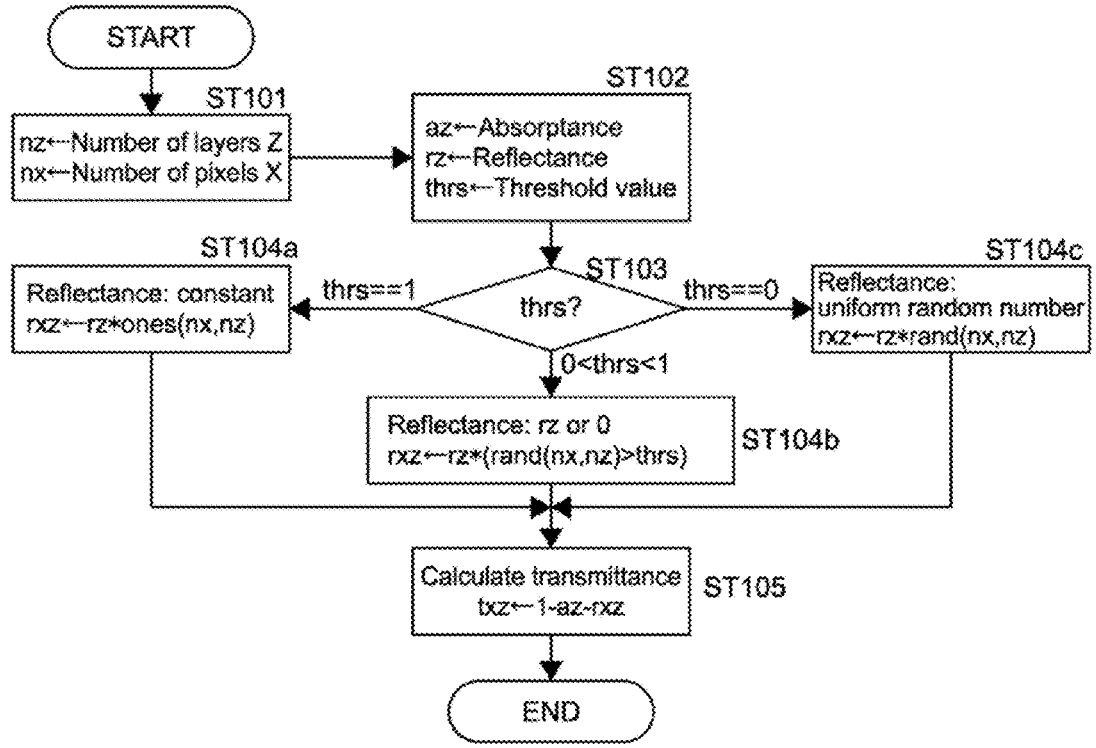
FIG. 5 is a flowchart for generating a reflectance distribution diagram of an XZ cross section.

5. Method of Generating Reflectance Distribution Diagram of XZ Cross Section FIG. 5 is a flowchart for generating a reflectance distribution diagram of an XZ cross section. First, the number of layers nz and the number of pixels nx in the x direction are designated (Step 101). Here, a threshold thrs is defined together with an absorptance az and a reflectance rz (Step 102). Further, for the sake of convenience of calculation, the following three reflectances can be set by using the threshold value thrs (Step 103).

(1) Constant at rz (thrs=1),
(2) Two values of 0 or rz (0<thrs<1),
(3) Uniform random number from 0 to rz (thrs=0)

Depending on these settings of thrs, an array of nx×nz in which all is 1 or an array of uniform random number is generated using Matlab's function ones or rand, and the following three arrays are calculated. Then, the reflectances of the above-mentioned (1) to (3) are stored in a two-dimensional array rxz of nx×nz.

In the above-mentioned (1), an array with rz*ones(nx,nz) in which the reflectance is constant at rz (Step 104a)

In the above-mentioned (2), a two-value array (Step 104b) with rz*(rand(nx,nz)>thrs) in which the reflectance is rz or 0

In the above-mentioned (3), an array with rz*rand(nx,nz) in which the reflectance is a uniform random number in the range of 0 to rz (Step 104c)

Figure 6A:
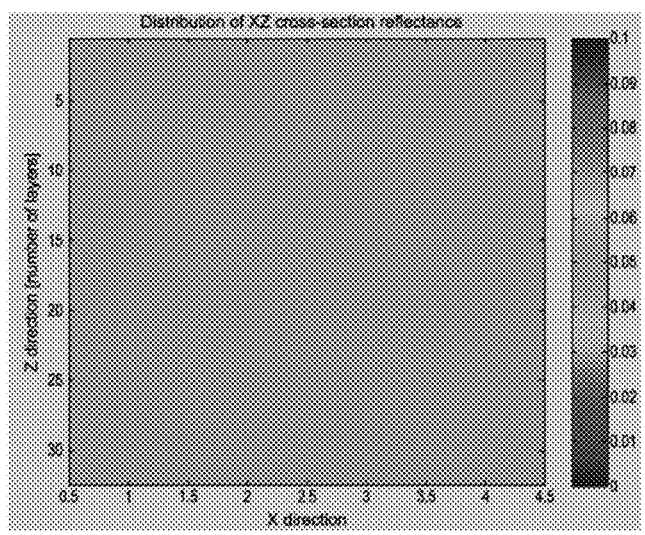
FIGS. 6A, 6B and 6C show two-dimensional arrays of thus obtained three kinds of reflectances of nx×nz, for example.
Figure 6B:
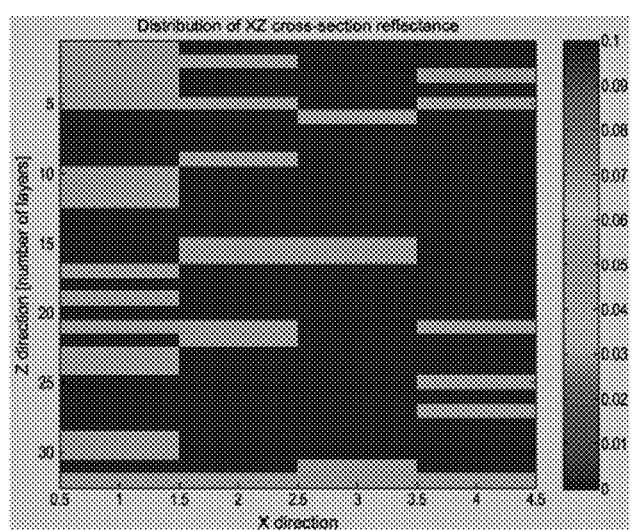
Figure 6C:
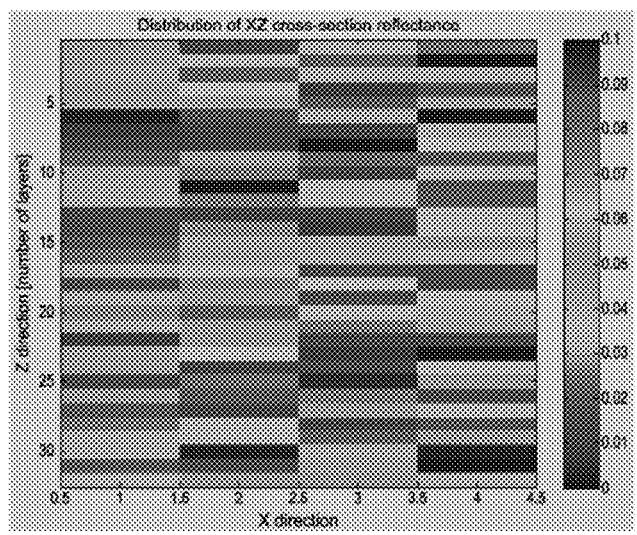

FIGS. 6A, 6B and 6C show two-dimensional arrays of thus obtained three kinds of reflectances of nx×nz, for example. Here, nz=32 and nx=4 are set. FIG. 6A corresponds to the above-mentioned (1), FIG. 6B corresponds to the above-mentioned (2), and FIG. 6C corresponds to the above-mentioned (3). For example, rz=0.05 in FIG. 6A, rz=0 or 0.05 in FIG. 6B, and it was random in the range of r=0 to 0.05 in FIG. 6C. The absorptance a was 0.05 in all of FIGS. 6A, 6B and 6C. The transmittance t was 0.9 in FIG. 6A, two values of 0.9 and 0.95 in FIG. 6B, and random in the range of 0.9 to 0.95 in FIG. 6C.

In FIGS. 6A, 6B and 6C, the vertical graph on the right side shows the criteria of intensity divided for each color. The distribution (not considering absorptance and transmittance) indicated by a two-dimensional array of reflectance obtained only by simple reflection is referred to as "original reflectance distribution model" in this specification.

Note that it is also possible for the applicant to submit colored FIGS. 6A, 6B and 6C in response to requests from the Government or the Bureau. This also applies to FIGS. 8A, 8B and 8C, FIGS. 11A, 11B and 11C, and other grayscale images.

Finally, the calculation txz=1−az−rxz is performed and a transmittance txz is calculated (Step 105). Thus, a two-dimensional array of transmittance of nx×nz can be obtained. Note that a three-dimensional array of transmittance of nx×nz is not shown. In the following, as a signal to be originally acquired, a method of calculating a signal (considering transmittance and absorptance) obtained by the simple reflection obtained in Step 105 will be described. Note that the above-mentioned "original reflectance distribution model" is not a signal that is to be originally acquired but represents distribution represented by a two-dimensional array of reflectance.

6. Method of Calculating Energy of Simple Reflection (or Intensity Thereof)

Figure 7:
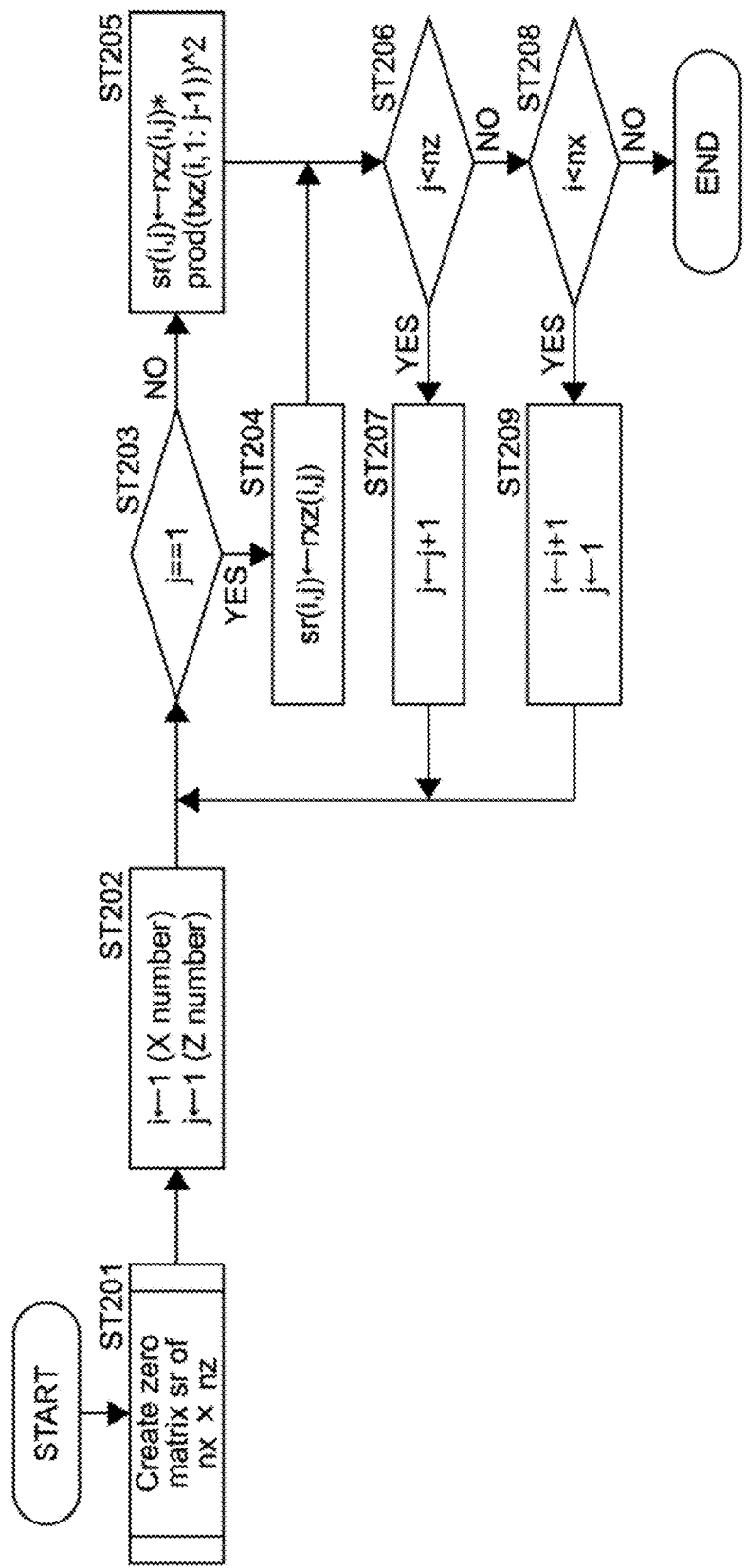
FIG. 7 is a flowchart showing a method of calculating simple reflection.

Now, the reflectance distribution (or energy distribution) of simple reflection that is the signal (considering transmittance and absorptance) to be originally acquired will be described. FIG. 7 is a flowchart showing a method of calculating simple reflection that is the signal to be originally acquired. In FIG. 7, sr(nx,nz) means reflected energy distribution.

First, a two-dimensional array sr of nx×nz in which all elements are 0 is created (Step 201). Both a number i in the x direction and a number j in the z direction are initialized to 1 (Step 202). In the case where j=1 in the highest layer (surface layer) (YES in Step 203), rxz(i,1) directly enters sr(i,1) (step 204). In the case where j>1 (NO in Step 203), rxz(i,j)*prod(txz(i,1:j−1))^2 is calculated (Step 205). This is equivalent to the equation 16 described with reference to FIG. 4, and is a value using the transmittance txz obtained in Step 105.

That is, in Steps 203 and 205, the signal intensity of the simple reflection of the n-th layer is calculated on the basis of the reflectance of the n-th layer and the transmittance of the n−1-th layer among the plurality of layers.

After Step 205, Steps 203 to 207 are repeated until the value of j is incremented one by one to be nz. When j=nz, i is incremented by 1, then j is initialized to 1, and Steps 203 to 206, 208, and 209 are repeated. It finishes when the calculation where j=nz and i=nx is finished.

In this embodiment, the signal intensity (reflection power) obtained by simple reflection up to, for example, nx=15 is shown below. For simplicity, sr(i,j), rxz(i,j), and txz(i,j) are respectively represented by s(j), r(j), and t(j).

$s(1)=r(1)$ $s(2)=t(1))^2$ $s(3)=t(2)*t(1))^2$ $s(4)=t(3)*t(2)*t(1))^2$ $s(5)=t(4)*t(3)*t(2)*t(1))^2$ $s(6)=t(5)*t(4)*t(3)*t(2)*t(1))^2$ $s(7)=t(6)*t(5)*t(4)*t(3)*t(2)*t(1))^2$ $s(8)=t(7)*t(6)*t(5)*t(4)*t(3)*t(2)*t(1))^2$ $s(9)=t(8)*t(7)*t(6)*t(5)*t(4)*t(3)*t(2)*t(1))^2$ $s(10)=t(9)*t(8)*t(7)*t(6)*t(5)*t(4)*t(3)*t(2)*t(1))^2$ $s(11)=t(10)*t(9)*t(8)*t(7)*t(6)*t(5)*t(4)*t(3)*t(2)*t(1))^2$ $s(12)=t(11)*t(10)*t(9)*t(8)*t(7)*t(6)*t(5)*t(4)*t(3)*t(2)*t(1))^2$ $s(13)=t(12)*t(11)*t(10)*t(9)*t(8)*t(7)*t(6)*t(5)*t(4)*t(3)*t(2)*t(1))^2$ $s(14)=t(13)*t(12)*t(11)*t(10)*t(9)*t(8)*t(7)*t(6)*t(5)*t(4)*t(3)*t(2)*t(1))^2$ $s(15)=t(14)*t(13)*t(12)*t(11)*t(10)*t(9)*t(8)*t(7)*t(6)*t(5)*t(4)*t(3)*t(2)*t(1))^2$

Figure 8A:
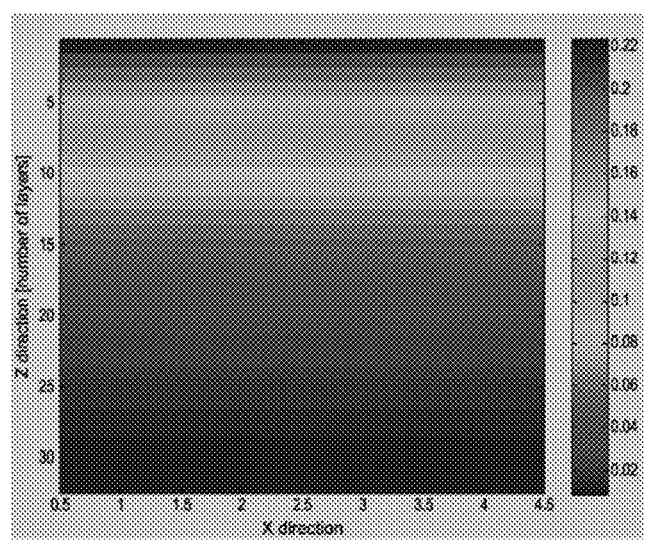
FIGS. 8A, 8B and 8C each show a signal of simple reflection obtained by calculation according to the flowchart shown in FIG. 7, taking transmittance and absorptance into account.
Figure 8B:
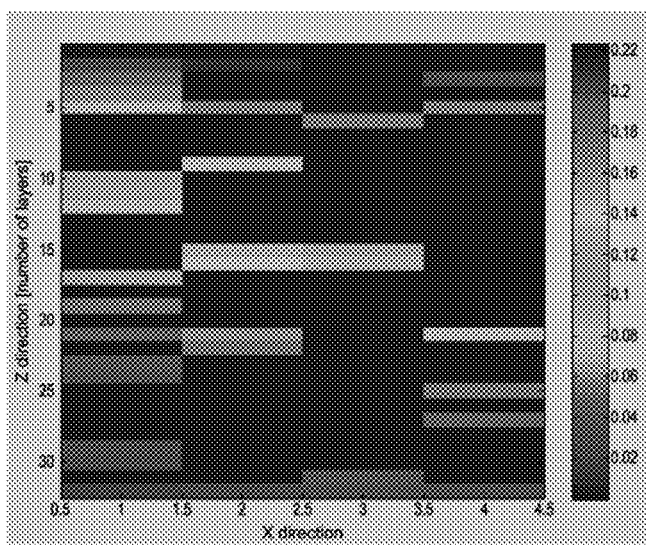
Figure 8C:
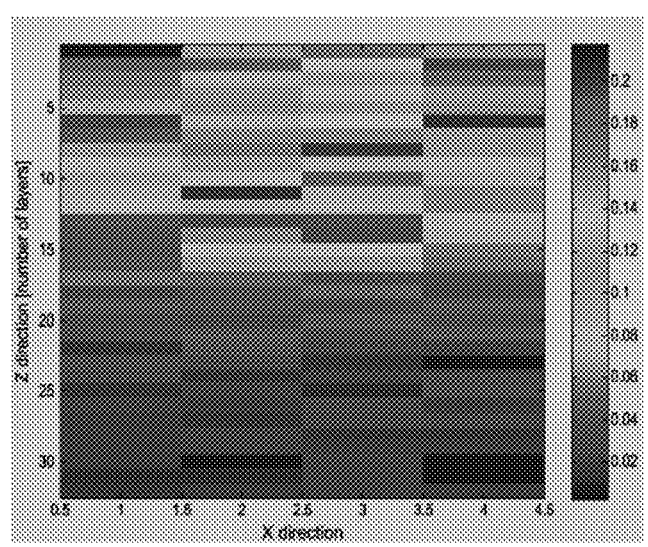

FIGS. 8A, 8B and 8C show simple reflection considering transmittance and absorptance obtained by the calculation according to the flow chart shown in FIG. 7, i.e., a signal to be originally acquired. FIG. 8A shows a case where the reflectance is constant (rz), FIG. 8B shows a case where the reflectance is two values (0 or rz), and FIG. 8C shows a case where the reflectance is a uniform random number.

Here, nz=32 and nx=4 are set. For example, rz=0.05 in FIG. 8A, rz=0 or 0.05 in FIG. 8B, and it was random in the range of r=0 to 0.05 in FIG. 8C. The absorptance a was set to 0.05 in all of FIGS. 8A, 8B and 8C. The transmittance t was 0.9 in FIG. 8A, two values of 0.9 and 0.95 in FIG. 8B, and random in the range of 0.9 to 0.95 in FIG. 8C.

Note that the calculated two-dimensional array sr shows the distribution of reflected energy as described above, and corresponds to f(x) described in the basic principle of the FD-SS OCT. Therefore, in FIGS. 8A, 8B and 8C, sqrt(sr) that is the square root of sr is calculated and shown as intensity (power) (refer to the equation 3). For example, the intensity when the reflectance is r=0.05 is 0.22. It can be seen that in FIGS. 8A, 8B and 8C, as the nz is larger (deeper), the intensity is decreased and the contrast is reduced.

7. Method of Calculating Energy of Multiple Reflection (or Intensity Thereof)

Next, multiple reflection as noise, here, triple reflection will be described.

FIGS. 9A, 9B and 9C are diagrams for considering a method of specifically calculating a signal due to triple reflection. For example, a case where triple reflection (FIG. 9B) having the same optical path length as the optical path length in the case of simple reflection at the j-th layer (FIG. 9A) occurs will be considered.

The number of layers transmitted or reflected is considered to correspond to the optical path length. As shown in FIG. 9A, when considering simple reflection in the layer, it is transmitted through the layers from the first layer to the j−1-th layer twice in the forward path and the backward path. In this case, the optical path length is 2*(j−1)+1=2*j−1.

As shown in FIG. 9B, in the case of triple reflection, the optical path length is 1+2*(j−k−1)+1+1+2*(k−1)=1+2*(j−1) in the case where first reflection (#1) occurs at the j−k-th layer just above the j-th layer by k layers, second reflection (#2) occurs at the j−k-m-th layer just thereabove by m layers, and third reflection (#3) occurs at the j−m-th layer. Therefore, it can be seen that the triple reflection has the same optical path length as the simple reflection.

In order to calculate the signal obtained by this triple reflection, as shown in FIG. 9C, it is easy to understand by decomposing triple reflection into simple reflection. That is, the energy of simple reflection at the j−k-th layer where the first reflection (#1) occurs is sr(j−k), and the reflection at the j−k-m-th layer where the second reflection (#2) occurs is rxz(i,j−k−m). Further, the reflection at the j−m-th layer where the third reflection (#2) occurs is rxz(j−m), and the influence of the transmittance going back and forth between the reflection (#2) and the reflection (#3) is represented by (prod(txz(i,j−k−m+1:j−m−1))^2.

Figure 10:
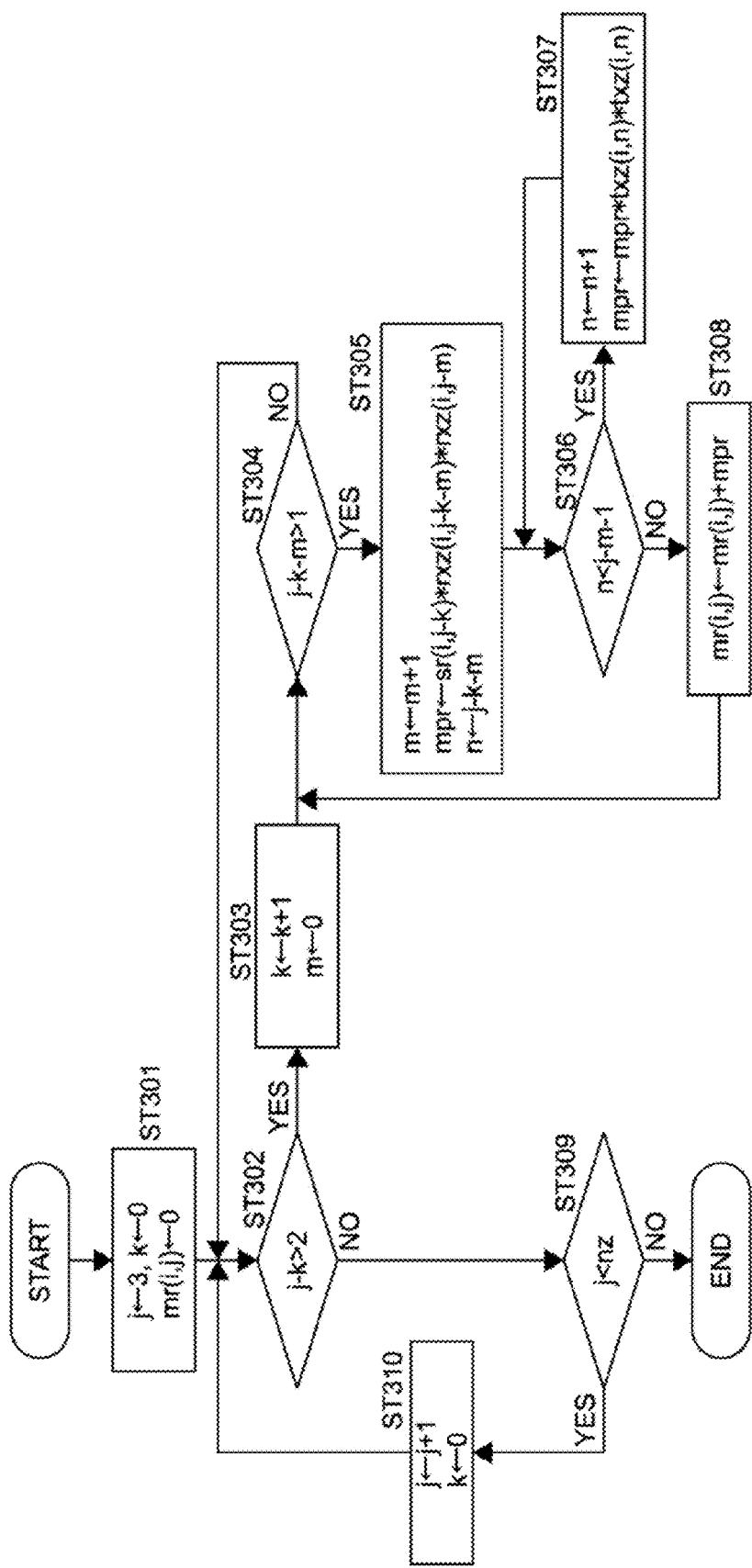
FIG. 10 is a flowchart showing a method of calculating triple reflection.

FIG. 10 is a flowchart showing a method of calculating triple reflection. First, mr is created as a two-dimensional array of nx×nz for storing the energy of triple reflection (Step 301). In order to simplify the description, i is fixed, and it is started by setting mr(i,j) to 0. Further, since triple reflection occurs only at a layer deeper than the third layer, the number j in the z direction is initialized to 3, and a parameter k, which indicates that the first reflection occurs at a layer shallower than the layer of simple reflection by k layers, is initialized to 0 (step 301).

Next, j−k>2, which is a condition for enabling triple reflection, is checked (Step 302). In the case where the relationship of jk>2 is established, k is incremented by 1, and m, which is the number of layers passed through between the first reflection and the second reflection, is initialized to 0 (Step 303). The relationship of j−k−m>1, which is a condition for the layer of the second reflection to be deeper than the first layer, is checked (Step 304). In the case where the relationship of j−k−m>1 is established, m is incremented by 1, and mpr=sr(i,j−k)*rxz(i,j−k−m)*rxz(i,j−m)=sr(1,2)*rxz(1,1)*rxz(i,2) is calculated (Step 305).

That is, Step 305 represents that the path of triple reflection is decomposed into the path of simple reflection, and the triple reflection is simulated by simple reflection, as described above with reference to FIGS. 9A, 9B and 9C. Hereinafter, this simple reflection may be referred to as "pseudo simple reflection" as necessary for convenience of description.

sr(i,j−k) represents the energy at the time of simple reflection at the j−k-th layer. The second reflectance at the j−k-m-th layer is represented by rxz(i,j−k−m), and the third reflectance at the j−m-th layer is represented by rxz(i,j−m). In Step 305, n=j−k−m is a parameter for considering the attenuation due to the transmittance of the layers passed through between the second reflection and the third reflection. While the relationship of n<j−m−1 is established (until just before the relationship of n=j−m−1 is established), it is calculated by being multiplied by the transmittance txz (i,n) (YES in Step 306, Step 307).

When the relationship of n=j−m−1 is established (NO in Step 306), since the energy mpr of triple reflection by one path is calculated, this is added to mr(i,j) (Step 308).

Steps 304 to 308 are repeated by incrementing m one by one 1 until j−k−m=1 (NO in Step 304) where the second reflection occurs at the first layer. In the case of NO in Step 304, it can be checked that the first reflection occurs above the j−1-th layer by j−k>2 (Step 302), k is incremented by 1 (Step 303), and thereafter, Steps 304 to 308 are repeated.

Thus, mr(i,j), which is the sum of signals (energy) due to triple reflection having the same optical path length as the optical path length of simple reflection of the j-th layer, can be obtained (Step 308).

In the case where the first reflection does not occur above the j−1-th layer (NO in Step 302), j<nz is checked (Step 309). When j is incremented one by one from 3 (Step 310) and repeated until j=nz, which is the range to be calculated (NO in Step 309), the calculation of mr(i,j) at a certain x position i is finished.

In the above processing, i is fixed as described above. Although omitted in FIG. 10, it is possible to finally obtain the signal mr(i,j) due to triple reflection by repeating the above-mentioned processing from i=1 to nx.

Note that mr represents energy similarly to sr. Therefore, the square root sqrt(mr) thereof can be calculated as signal intensity due to triple reflection.

The number of combinations of triple reflection having the same optical path length as that of the simple reflection at the j-th layer is represented by (j−1)*(j−2)/2 as described above. It is one by the third layer, and 21 by the eighth layer. Hereafter, it is 560 by the 16th layer, 4,960 by the 32nd layer, 41,644 by the 64th layer, and 341,376 by the 128th layer, and the total number of combinations is enormous.

8. Signal Obtained by Triple Reflection

Figure 11A:
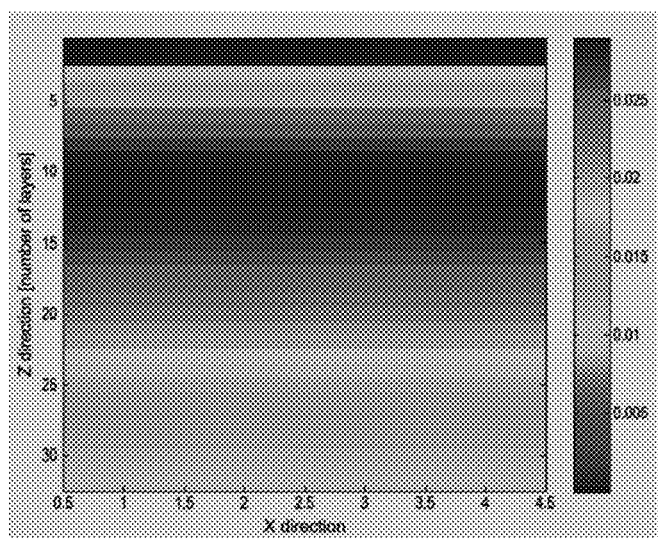
FIGS. 11A, 11B and 11C each show a signal of triple reflection obtained by calculation according to the flowchart shown in FIG. 10.
Figure 11B:
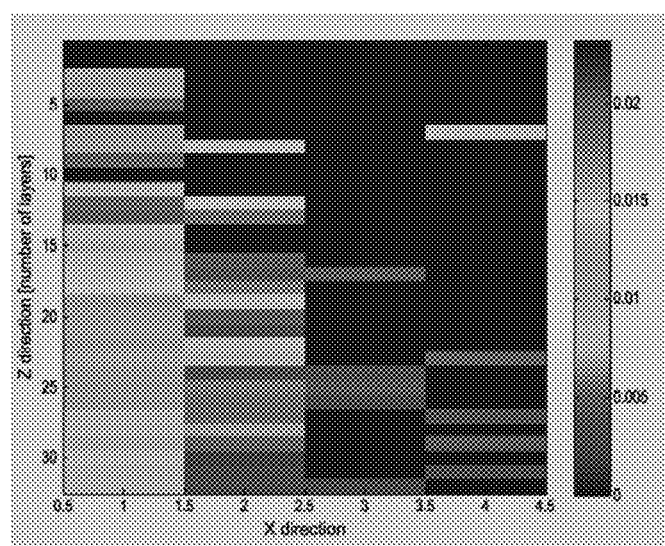
Figure 11C:
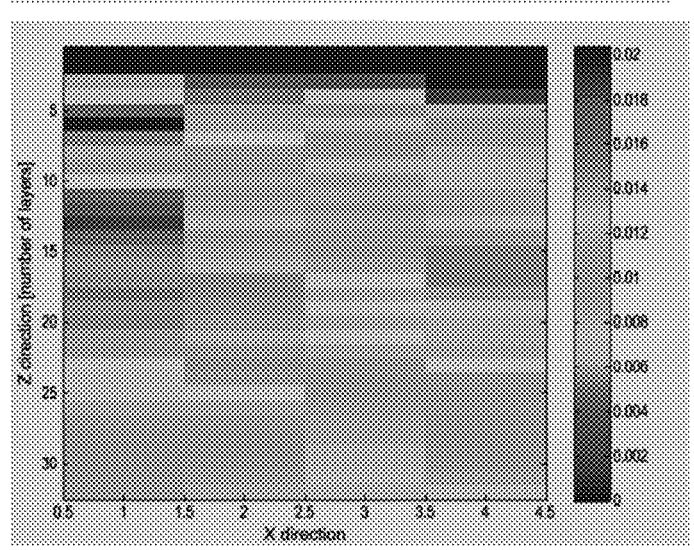

FIGS. 11A, 11B and 11C each show a signal of triple reflection (considering transmittance and absorptance) obtained by the calculation according to the flowchart shown in FIG. 10. FIG. 11A shows a case where the reflectance is constant (rz), FIG. 11B shows a case where the reflectance is two values (0 or rz), and FIG. 11C shows a case where the reflectance is a uniform random number. These signals are the intensity distribution sqrt(mr) represented as the square root of the energy mr similarly to FIGS. 8A 8B and 8C.

Here, nz=32 and nx=4 are set. For example, rz=0.05 in FIG. 11A, rz=0 or 0.05 in FIG. 11B, and it was random in the range of r=0 to 0.05 in FIG. 11C. The absorptance a was set to 0.05 in all of FIGS. 11A, 11B and 11C. The transmittance t was 0.9 in FIG. 11A, two values of 0.9 and 0.95 in FIG. 11B, and random in the range of 0.9 to 0.95 in FIG. 11C.

As shown in FIG. 8A, the magnitude of simple reflection is monotonously reduced as the depth is increased in the Z direction. In contrast, as shown in FIG. 11A, although the magnitude of triple reflection is small in a shallow layer, it tends to be rapidly increased as it gets deeper in the Z direction and then be gradually reduced. Referring to FIGS. 11B and 11C, a tendency similar to this is observed.

9. Combined Signal of Simple Reflection and Triple Reflection

Figure 12A:
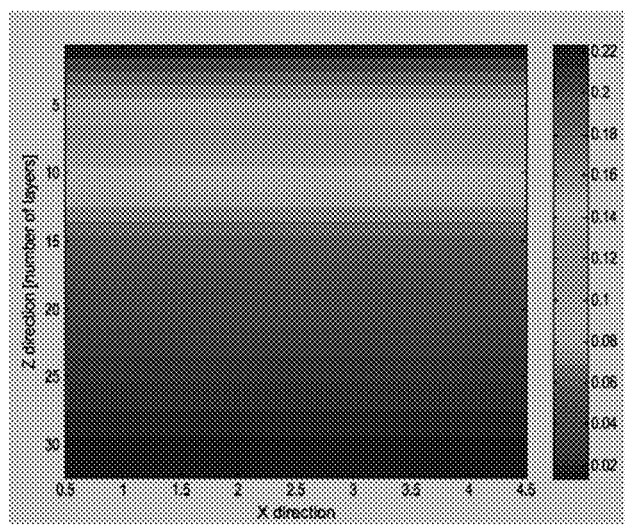
FIGS. 12A, 12B and 12C respectively show the combined intensity distribution of the intensity of simple reflection shown in FIGS. 8A, 8B and 8C and the intensity of triple reflection shown in FIGS. 11A, 11B and 11C.
Figure 12B:
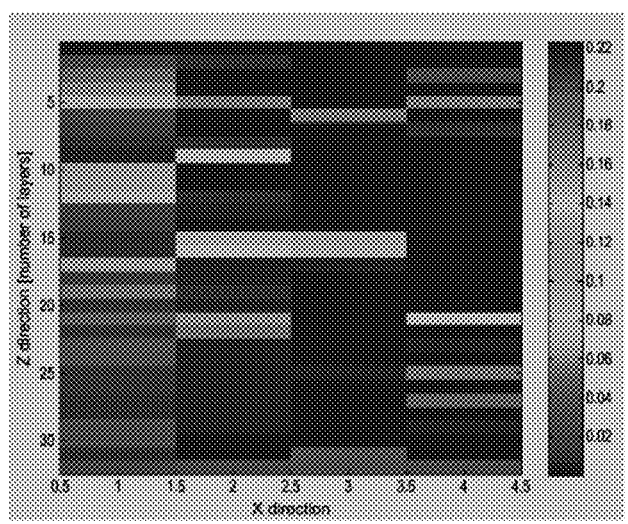
Figure 12C:
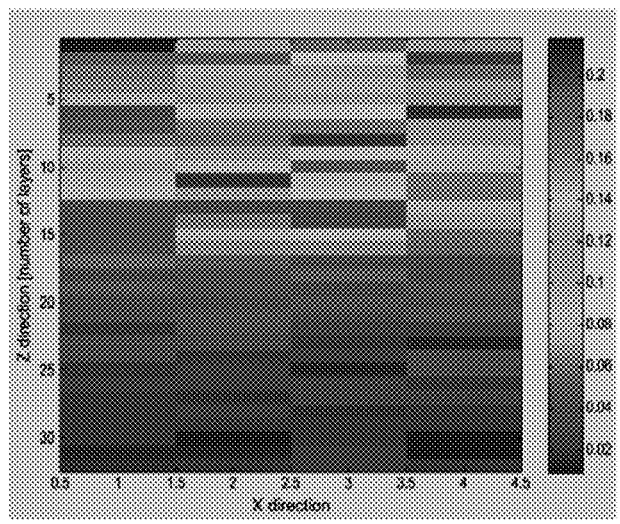

FIGS. 12A, 12B and 12C respectively show the combined intensity distribution sqrt(sr+mr) of the intensity of simple reflection shown in FIGS. 8A, 8B and 8C and the intensity of triple reflection shown in FIGS. 11A, 11B and 11C. FIG. 12A is a combination of FIG. 8A and FIG. 11A, FIG. 12B is a combination of FIG. 8B and FIG. 11B, and FIG. 12C is a combination of FIG. 8C and FIG. 11C. The combined intensity of simple reflection and triple reflection actually means the reflection intensity obtained by the optical detector of the optical tomographic measurement apparatus.

Figure 13:
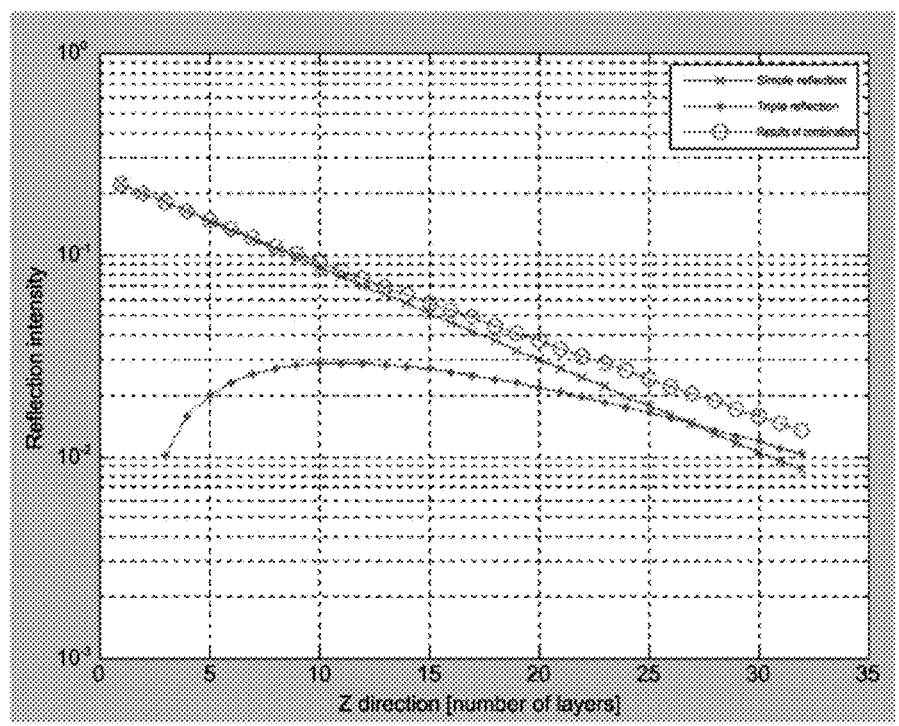
FIG. 13 corresponds to FIG. 12A, and shows the one-dimensional intensity distribution in the z direction of a signal of simple reflection, a signal of triple reflection, and a signal obtained by combining these signals.

10. One-Dimensional Intensity Distribution of Simple Reflection, Triple Reflection, and Combined Signals Thereof FIGS. 13 to 15 each show a one-dimensional intensity distribution in the z direction (e.g., the position in the x direction is fixed to i=1) of a signal of simple reflection, a signal of triple reflection, and a signal obtained by combining these signals. FIG. 13 corresponds to FIG. 12A, FIG. 14 corresponds to FIG. 12B, and FIG. 15 corresponds to FIG. 12C.

The signal to be originally acquired is a signal of simple reflection. However, since a signal of triple reflection is generated as noise as shown in FIGS. 13 to 15, theoretically, the combined signal of simple reflection and triple reflection is a signal detected by the photodetector as described above.

As shown in FIG. 13, in the 27th layer, simple reflection sqrt(sr) and triple reflection sqrt(mr) intersect with each other, where the influence of triple reflection is larger at a position deeper than this. That is, assuming that there is no other noise factor, the SN ratio is not more than 0 dB in the 27th layer and the deeper layers.

Figure 14:
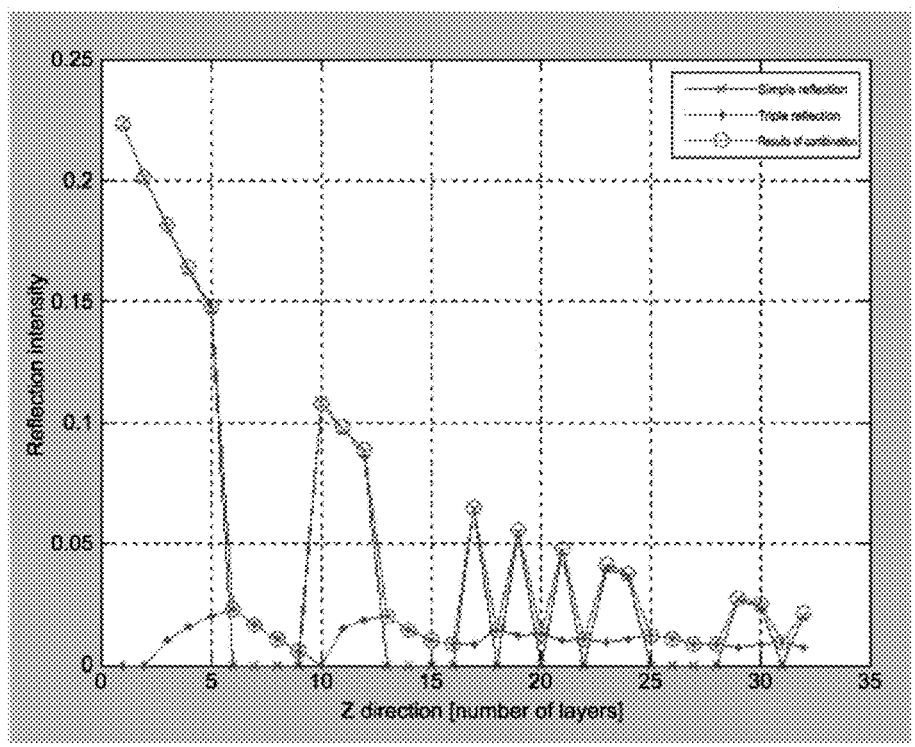
FIG. 14 corresponds to FIG. 12B, and shows the one-dimensional intensity distribution in the z direction of a signal of simple reflection, a signal of triple reflection, and a signal obtained by combining these signals.

As shown in FIG. 12B and FIG. 14, it can be seen that the SN ratio and the contrast are reduced due to the echo of the previous layer that has appeared at the place where there should be no signal originally.

Figure 15:
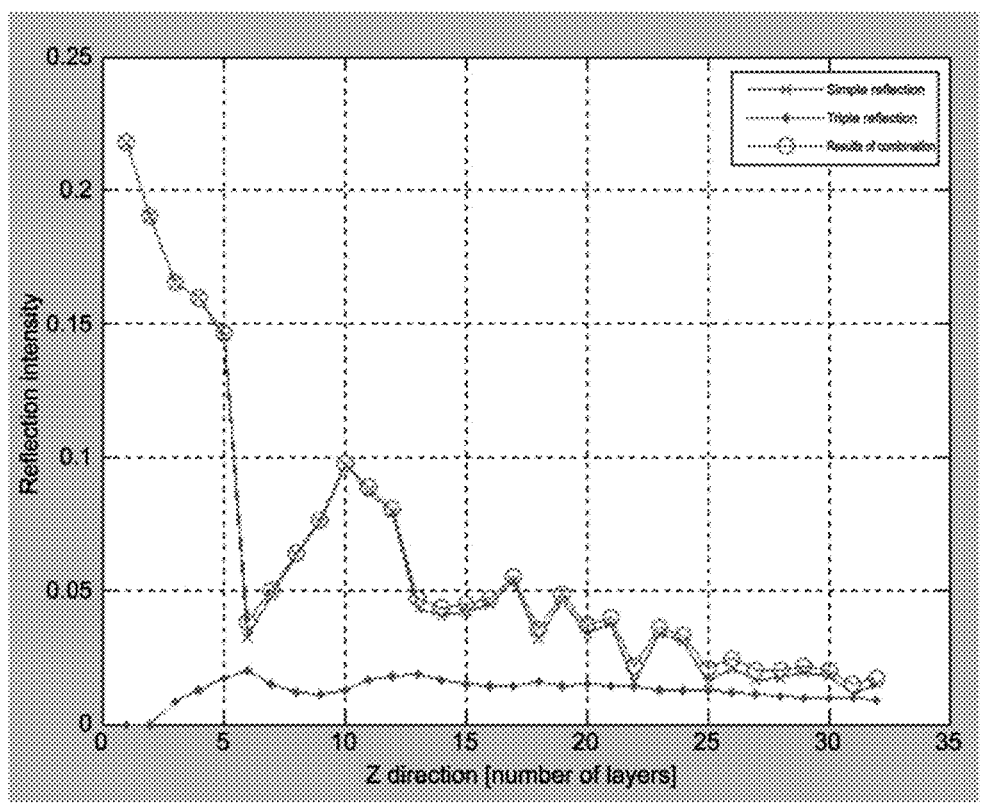
FIG. 15 corresponds to FIG. 12C, and shows the one-dimensional intensity distribution in the z direction of a signal of simple reflection, a signal of triple reflection, and a signal obtained by combining these signals.

As shown in Part of FIG. 12 and FIG. 15, it can be seen that the contrast is reduced as a whole due to the influence of triple reflection.

From the above, in the OCT, irrespective of the OCT method such as TD and FD, the SN ratio and the contrast are reduced due to the influence of multiple reflection, and it is only possible to see an image including noise, which is not the image that is desired to see.

11. Removal of Triple Reflection According to Embodiment of Present Technology The present technology is mainly based on the following three aims.

(1) Since there is no multiple reflection having the same optical path length as that of signals subjected to simple reflection at the first layer and the second layer, these two signals include no multiple reflection.

(2) Assuming that the absorptance is constant, the effects of multiple reflection included in a signal from the third and subsequent layers can be calculated from a signal of simple reflection at a shallower layer.

(3) By removing a signal of multiple reflection (here, triple reflection) from a signal of simple reflection (including pseudo simple reflection) from the third and subsequent layers, a signal of simple reflection from the third and subsequent layers can be obtained.

Figure 16:
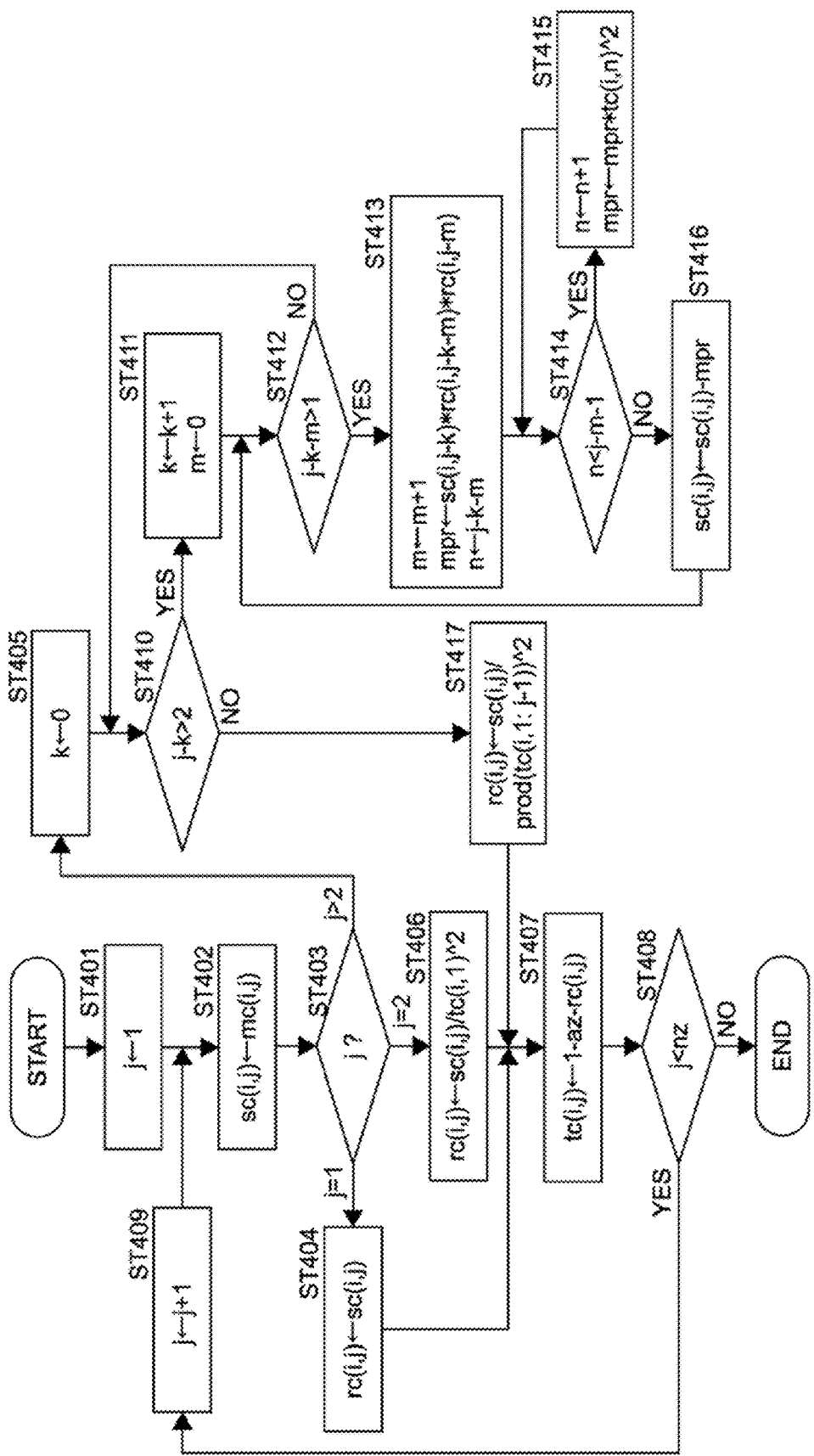
FIG. 16 is a flowchart showing a method of removing triple reflection, which is a main part of the present technology.

FIG. 16 is a flowchart showing a method of removing triple reflection, which is a main part of the present technology. In this flowchart, in order to simplify the description, the diagram of generation of a zero matrix rc (reflectance), tc (transmittance), and sc (reflection intensity to be corrected) of nx×nz, and the loop of i=1:nx in the x direction are omitted.

Further, a combined signal intensity mc of simple reflection and triple reflection is known as measurement result. That is, in the algorithm according to the present technology, a corrected reflection intensity sc is obtained by removing the signal intensity of triple reflection from the known combined intensity mc of simple reflection and triple reflection, which is obtained as a result of measurement by the optical tomographic measurement apparatus according to the present technology (that is, the signal intensity of interference light as return light). The corrected reflection intensity sc is specifically the intensity of simple reflection obtained as a result of correction (to be acquired).

Further, in this algorithm, also the reflectance rc of each layer can be obtained on the basis of the corrected simple reflection intensity sc and transmittance (and absorptance).

Hereinafter, with reference to FIG. 16, details of the calculation method will be described.

First, j indicating the layer number in the z direction is set to 1 (Step 401). The combined intensity mc(i,1) is assigned to the signal intensity sc(i,1) of simple reflection (Step 402). The magnitude of j is checked (Step 403). Now, since j=1, sc(i,1) can be used as it is for rc(i,1) (Step 404).

Calculation of tc(i,1)=1−az−rc(i,1) is performed using the constant absorptance az, and a transmittance tc(i,1) of the first layer to be used later is calculated (Step 407). This is the same processing as Step 105 shown in FIG. 5.

The magnitude of j is checked again (Step 408). Now, since j<nz, j is incremented by 1 to be 2 (Step 409).

Similarly, in the case of j=2, the combined intensity mc(i,2) is assigned to the intensity sc(i,2) of simple reflection. In the case of j=2, rc(i,2) can be obtained (Step 406) by dividing sc(i,2) by the square of tc(i,1) obtained earlier. Calculation of tc(i,2)=1−az−rc(i,2) is performed using the constant absorptance az to calculate the transmittance tc(i,2) of the second layer (Step 407).

The magnitude of j is checked again (Step 408). Now, since j<nz, j is incremented by 1 to be 3 (Step 409). Hereinafter, the case where j is not less than 3 (j>2) will be described. After that, processing is substantially the same as the flowchart shown in FIG. 10 except that the variable names are different.

First, the combined intensity mc (i,j) is assigned to the signal intensity sc (i,j) of simple reflection (Step 402). In the case of j>2, the parameter k, which indicates that the first reflection occurs at a layer shallower than the layer of simple reflection by k layers, is initialized to 0 (Step 405).

The gist of the processing of Steps 412 to 416 is the same as the gist of the processing of Steps 304 to 308 shown in FIG. 10. However, the processing of Step 416 is different from that of Step 308 in that a value obtained by subtracting the signal strength of triple reflection from the signal intensity of simple reflection including pseudo simple reflection is obtained as the corrected signal strength sc.

The condition j−k>2 for enabling triple reflection is checked (Step 410). In the case of j−k>2, k is incremented by 1, and m, which is the number of layers passed through between the first reflection and the second reflection, is initialized to 0 (Step 411). In the case where j−k−m>1 and the second reflection occurs at a position deeper than the first layer (YES in Step 412), m is incremented by 1, and calculation of mpr=sc(i,j−k)*rc(i,j−k−m)*rc(i,j−m) is performed (Step 413). That is, the triple reflection is replaced with simple reflection including pseudo simple reflection.

sc(i,j−k) represents the energy at the time of simple reflection at the j−k layer, and has already been calculated. Similarly, also the second reflection rc(i,j−k−m) at the j−k−m-th layer and the third reflection rc(i,j−m) at the j−m-th layer have already been calculated. The last parameter n=j−k−m is used to consider the attenuation due to the transmittance of the layers passed through between the second reflection and the third reflection.

In the case where n<j−m−1 (Step 414), calculation is performed by multiplying the square of the transmittance tc(i,n) that has been already calculated, by mpr (Step 415).

Since the energy mpr of triple reflection by one path is calculated when n=j−m−1 (NO in Step 414), this is subtracted from sc(i,j) (Step 416). By this Step 416, the triple reflection is removed.

Steps 412 to 416 are repeated by incrementing m one by one until j−k−m=1 (NO in Step 412) where the second reflection occurs at the first layer. In the case of NO in Step 412, it is checked by jk>2 (Step 410) that the first reflection occurs above the j−1-th layer, and by repeating the same thing, it is possible to obtain the signal intensity sc(i,j) of simple reflection by removing the signal of the triple reflection having the same optical path length as that of the simple reflection at the j-th layer (Step 416).

Finally, by dividing this sc(i,j) by the square prod(tc(i,1:j−1))^2 of the product of the transmittances from j=1 to j−1, it is possible to obtain a reflectance rc(i,j) at the j-th layer (Step 417). An image representing the distribution of this reflectance rc is an image of reflection directly observing the XZ cross section, i.e., an image of reflection (see FIGS. 6A, 6B and 6C) not considering the transmittance (and absorptance).

The processing of Steps 406 and 417 represents that the reflectance rc of the n-th (n is a natural number of not less than 2) layer is calculated on the basis of the signal intensity of simple reflection (see Step 416) from which the signal intensity of multiple reflection of the n-th layer is subtracted and transmittance of the n−1-th layer.

By incrementing j one by one from 3 and repeating the above calculation until j=nz (NO in Step 408), which is the range to be calculated, the calculation of the reflectance rc(i,j) at the certain x position i is finished.

Figure 17:
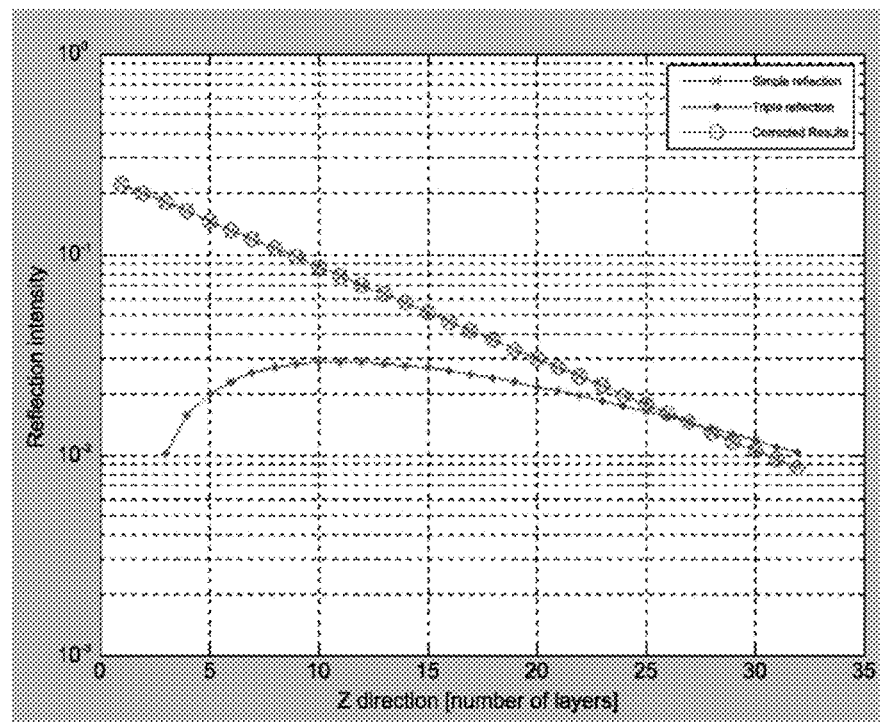
FIG. 17 shows the result of calculating the combined intensity distribution of simple reflection and triple reflection, and shows the result of applying the algorithm of the present technology to FIG. 12A.
Figure 18:
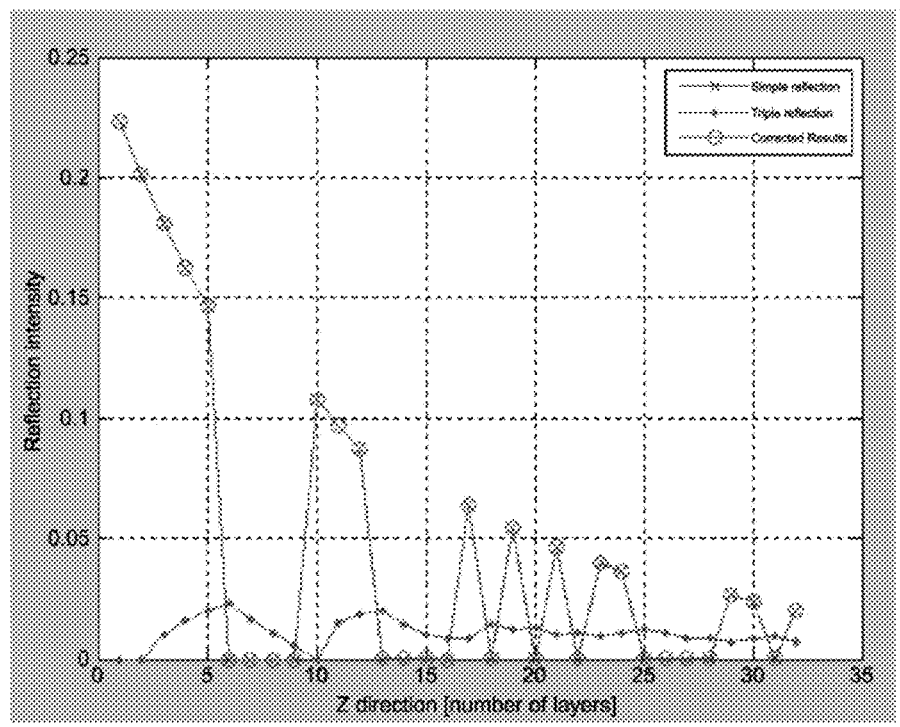
FIG. 18 shows the result of calculating the combined intensity distribution of simple reflection and triple reflection, and shows the result of applying the algorithm of the present technology to FIG. 12B.
Figure 19:
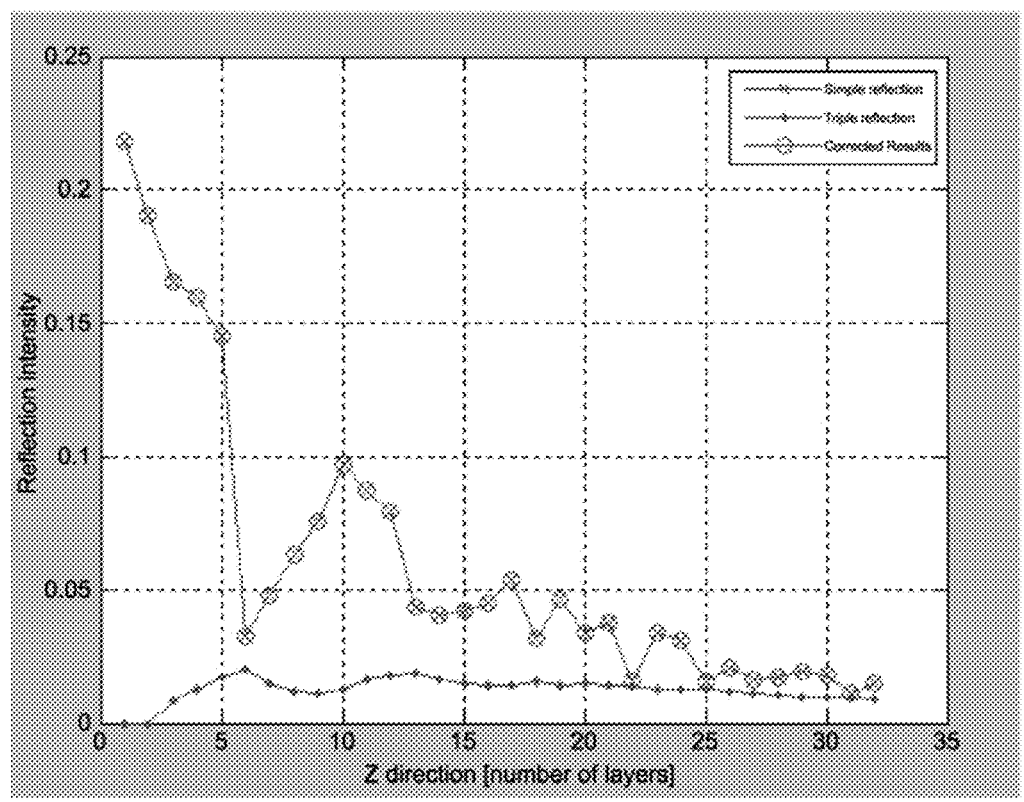
FIG. 19 shows the result of calculating the combined intensity distribution of simple reflection and triple reflection, and shows the result of applying the algorithm of the present technology to FIG. 12C.

FIGS. 17 to 19 each show the result of calculating the combined intensity distribution of simple reflection and triple reflection. FIGS. 17 to 19 respectively show the results of applying the algorithm shown in FIG. 16 to FIGS. 12A, 12B and 12C. Similarly to FIGS. 13 to 15, these figures show the intensity distribution in the Z direction at the position of i=1 (fixed) in the x direction. The combined intensity distribution of simple reflection and triple reflection actually corresponds to the signal strength mc. Note that in FIGS. 17 to 19, data of simple reflection and triple reflection is also included.

Although calculation based on the same assumption is performed in any of FIGS. 17 to 19, the effect of triple reflection is removed, and a signal of simple reflection can be obtained as expected. That is, it can be seen that the same results are obtained in FIGS. 13 to 15 and FIGS. 17 to 19. In the existing OCT system, it has been inevitable that the contrast is reduced and the SN ratio is also reduced as the measurement position becomes deeper. However, by using the algorithm according to the present technology, a signal of simple reflection with improved SN ratio can be obtained.

Further, according to the present technology, it is possible to perform efficient noise removal without requiring a procedure for acquiring artifacts by multiple reflection as in Patent Literature 1.

Further, by calculating the reflectance rc and the transmittance tc on the assumption that the absorptance is constant and displaying the reflectance rc (the value calculated in Steps 406 and 417) instead of displaying the intensity distribution, it is possible to obtain a clear image with high contrast and high SN ratio, which corresponds to direct observation of the XZ cross section. In the simulation of this time, the image showing the reflectance rc matched with the XZ cross-sectional images shown in FIGS. 6A, 6B and 6C. That is, the image of the reflectance distribution after applying the algorithm according to the present technology to the combined intensity mc of simple reflection and triple reflection set as a known measurement result was obtained as the original reflectance distribution model shown in FIGS. 6A, 6B and 6C.

The arithmetic amount and effect of the algorithm according to the present technology depend on the number of layers in the depth direction, the transmittance and the reflectance of the measurement object, and the like. Using the following equation 21, the number of times of possible triple reflection up to the n-th layer is calculated.

$$\sum_{m=1}^{n}\sum_{k=1}^{m-2} k = \sum_{m=1}^{n} \frac{m^2 - 3m + 2}{2} \qquad \text{[Math. 21]}$$

The calculation results of the number of times of possible triple reflection according to the equation 21 are as follows.
In the case where the number of layers is 16, 560
In the case where the number of layers is 32, 4960
In the case where the number of layers is 64, 41664
In the case where the number of layers is 128, 341376
In the case where the number of layers is 256, 2763520
In the case where the number of layers is 512, 22238720
In the case of measuring up to the 256th layer, i.e., in the case where the number of pixels in the depth direction is 256, it is necessary to calculate more than 2.76 million patterns.

In the above, the magnitude of the reflectance rz has been set to 0.05 (other than 0). FIGS. 20A, 20B, 20C and 20D and FIGS. 21A, 21B, 21C and 21D show the calculation result of the simple reflection intensity sc after correction in the case where the magnitude of the reflectance is changed from 0.02 to 0.002 which is smaller than that and the transmittance and absorptance are also reduced along with this. FIGS. 20A, 20B, 20C and 20D 0 show the case where the reflectance is constant, and FIGS. 21A, 21B, 21C and 21D show the case where the reflectance is two values.

Figure 20:
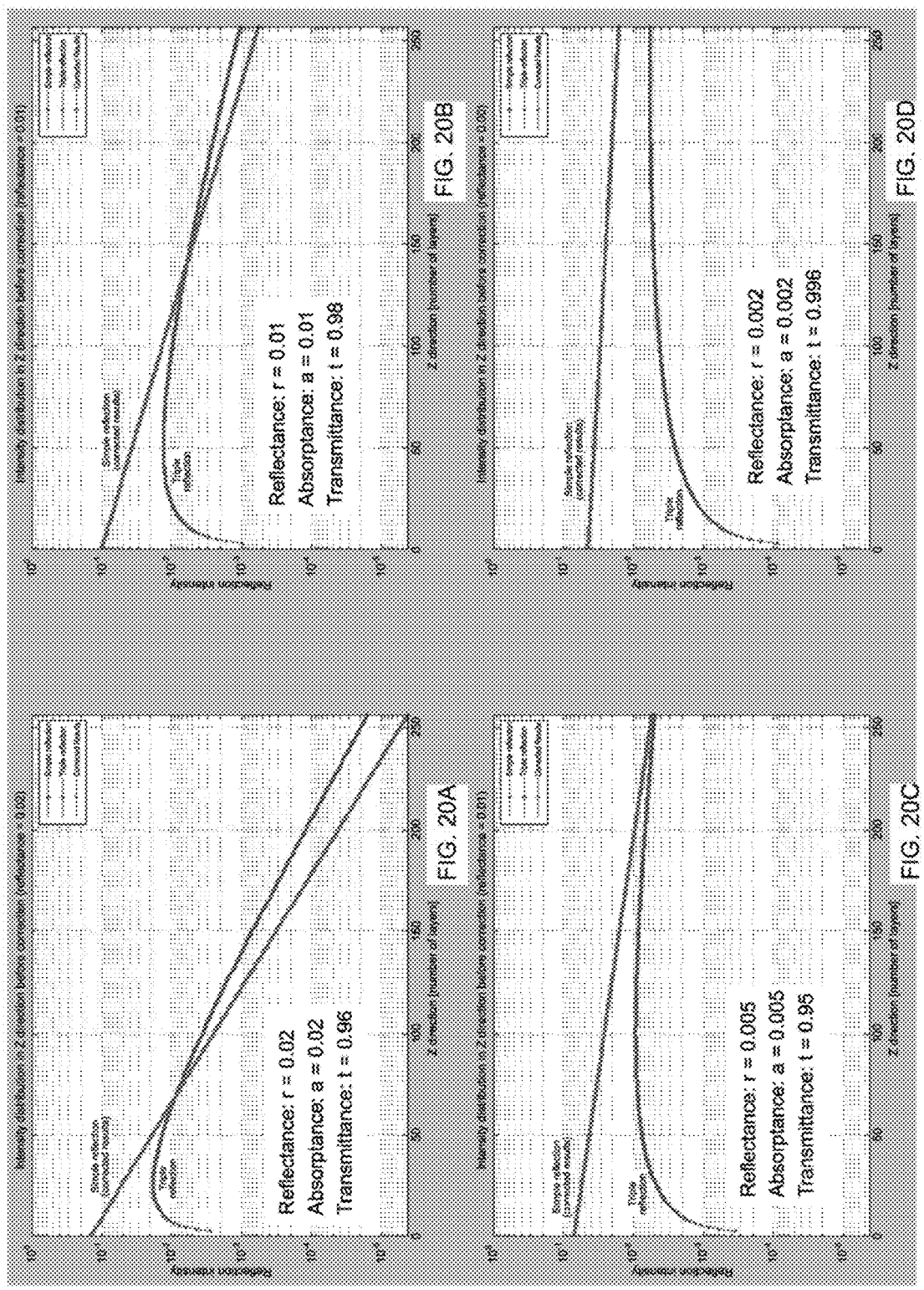
FIGS. 20A, 20B, 20C and 20D each show the result of calculating the reflected signal intensity after correction in the case where the magnitude of reflectance is changed (reflectance is constant in each diagram).
Figure 21:
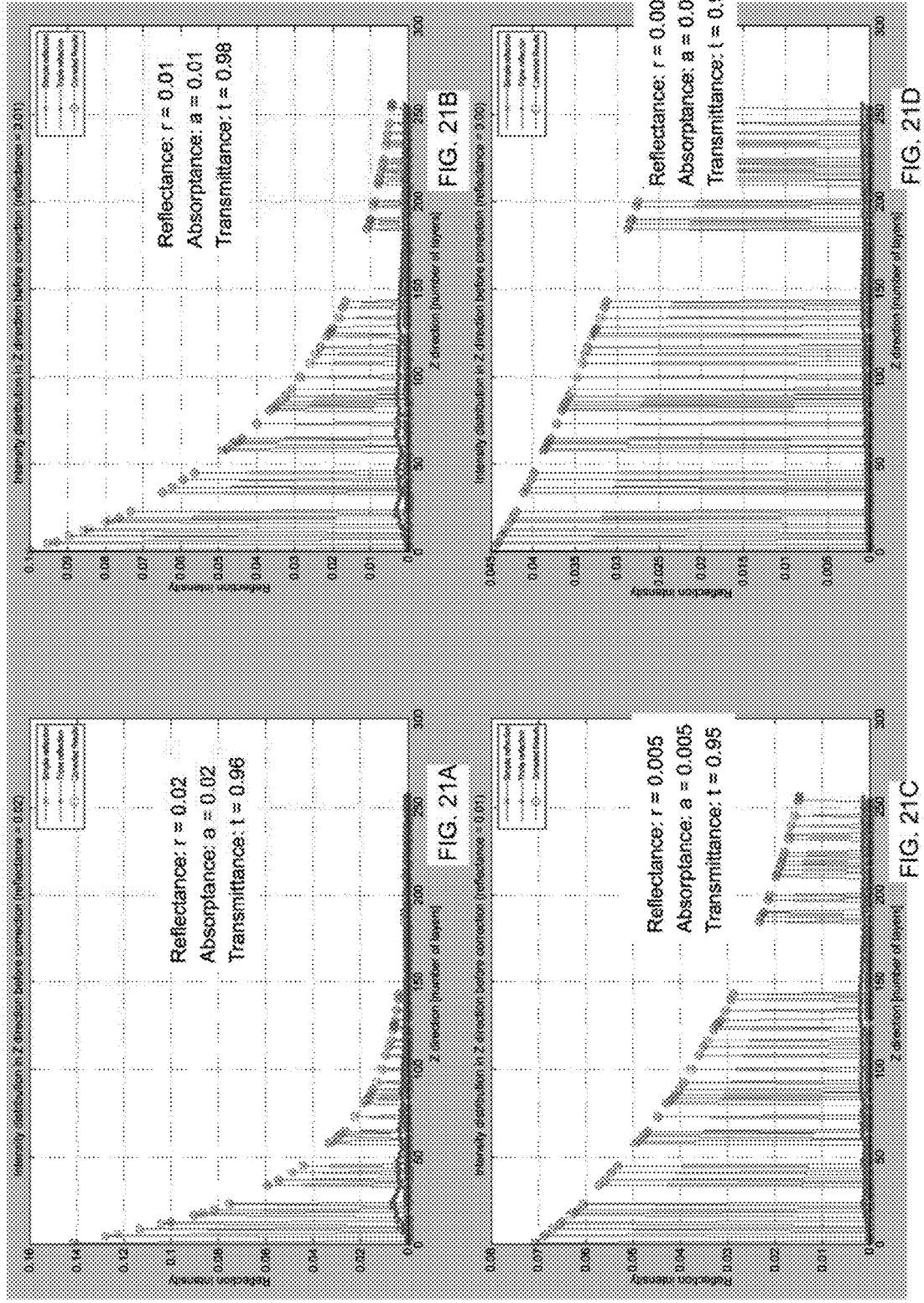
FIGS. 21A, 21B, 21C and 21D each show the result of calculating the reflected signal intensity after correction in the case where the magnitude of reflectance is changed (reflectance has 2 values in each diagram).

The reflectance r, the absorptance a, and the transmittance t were set as follows.
FIG. 20A and FIG. 21A: r=0.02, a=0.02, t=0.96
FIG. 20B and FIG. 21B: r=0.01, a=0.01, t=0.98
FIG. 20C and FIG. 21C: r=0.005, a=0.005, t=0.95
FIG. 20D and FIG. 21D: r=0.002, a=0.002, t=0.996

As a matter of course, since in the case where the reflectance and the transmittance are small, deterioration of the contrast and the SN ratio at the time of measuring the deep position becomes small, the effect of the present technology is also reduced. In the calculation at this time, it has been found that the effect of the present technology is great in the case where the reflectance is not less than 0.01.

Figure 22:
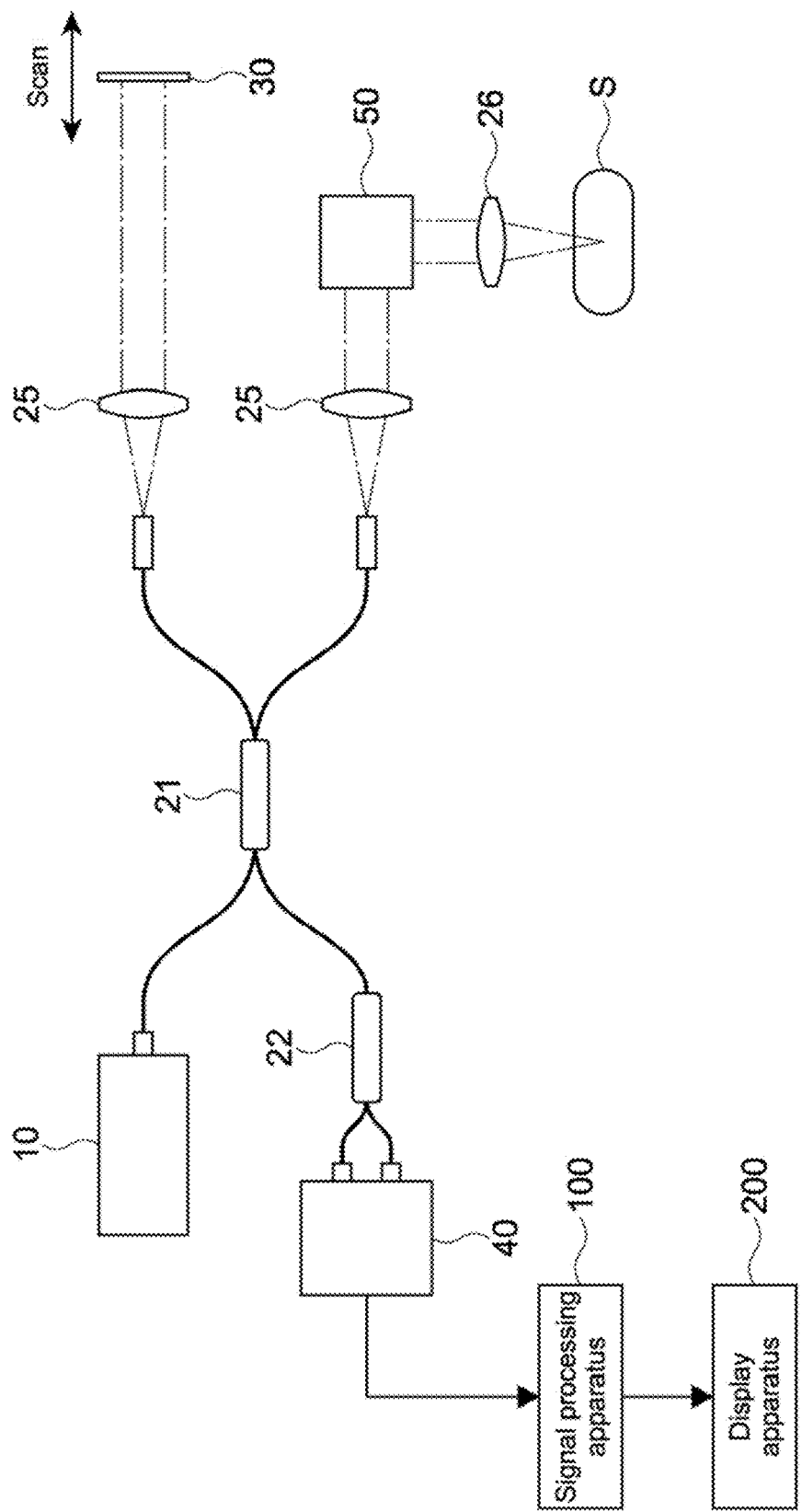
FIG. 22 shows an example of a configuration of an optical tomographic measurement apparatus to which a signal processing apparatus that realizes the above-mentioned algorithm of the present technology is applied.

12. Configuration Example of Optical Tomographic Measurement Apparatus According to Present Technology FIG. 22 shows an example of a configuration of an optical tomographic measurement apparatus to which a signal processing apparatus 100 that realizes the above-mentioned algorithm according to the present technology is applied. This optical tomographic measurement apparatus uses an optical fiber optical system and includes a light source 10, fiber couplers 21 and 22, collimator lenses 25, a reference mirror 30, a galvanometer scanner 50, an objective lens 26, a differential detector 40, and the signal processing apparatus 100.

The fiber coupler 21 has a function of demultiplexing light from the light source 10 into the collimator lenses 25, 25, and combining reference light from the reference mirror 30 and return light from the measurement object S to output the combined light to the fiber coupler 22. Typically, the galvanometer scanner 50 is configured to be capable of scanning light in two axes orthogonal to the z direction (the depth direction of the measurement object S).

The fiber coupler 22 demultiplexes interference light of the reference light and the return light output from the fiber coupler 21. The differential detector 40 has a function of outputting the differential of the interference light branched and output from the fiber coupler 22.

The signal processing apparatus 100 includes, for example, an arithmetic unit for realizing the above-mentioned algorithm according to the present technology. That is, the arithmetic unit is configured to calculate the signal intensity of simple reflection, which is one time of reflection of each of a plurality of layers of the measurement object, and calculate the signal strength of multiple reflection, which is the signal intensity of return light generated by being reflected three or more times in a plurality of layers, on the basis of the signal intensity of simple reflection. Specifically, the arithmetic unit is configured to calculate signal intensities of multiple reflection of the third and subsequent layers on the basis of the pseudo simple reflection that occurs by decomposing the path of triple reflection that occurs in the third and subsequent layers among the plurality of layers into the path of simple reflection.

The signal processing apparatus 100 typically includes hardware such as a CPU (Central Processing Unit), a RAM (Random Access Memory), and a ROM (Read Only Memory) for configuring a computer. Further, the signal processing apparatus 100 includes software for causing this computer to realize the above-mentioned calculation algorithm. In this case, the arithmetic unit mainly includes the CPU and the above-mentioned software. Instead of or in addition to the CPU, the arithmetic unit may include hardware such as a DSP (Digital Signal Processor) and a PLD (Programmable Logic Device).

A display apparatus 200 has a function of displaying the intensity distribution of the signal of simple reflection generated by the signal processing apparatus 100 as a one-dimensional (z-direction) graph or a two-dimensional (XZ cross-sectional) image.

13. Various Other Embodiments

The present technology is not limited to the above-mentioned embodiment, and various other embodiments can be realized.

The measurement object to be measured by the optical tomographic measurement apparatus according to the above-mentioned embodiment is not limited to biological tissues and cells, and may be inorganic materials.

The calculation algorithm by the signal processing apparatus 100 according to the above-mentioned embodiment does not depend on methods such as TD, FD-SD, and FD-SS, and the present technology is applicable to any of the methods.

In the calculation algorithm according to the above-mentioned embodiment, although the absorptance of each layer of the measurement object is set to be constant, the absorptance may be set so as to be fluctuated by a predetermined function for each layer.

In FIG. 22, for example, the signal processing apparatus 100 may be connected to the signal processing apparatus 100 via a WAN (Wide Area Network) or a LAN (Local Area Network).

For example, the system may be established so that the processing by the signal processing method according to the present technology is performed by a plurality of computers or a plurality of arithmetic units.

It should be noted that the present technology may take the following configurations.

(1)

A signal processing apparatus for an optical tomographic measurement apparatus that generates measurement light and reference light and measures a tomographic structure of a measurement object on the basis of a signal intensity of interference light between the reference light and return light of the measurement light from the measurement object, the signal processing apparatus including:

an arithmetic unit configured to calculate a signal intensity of simple reflection among the return light of the measurement light, the simple reflection being one time of reflection at a plurality of layers virtually set in a depth direction from a surface layer side of the measurement object, and calculate a signal intensity of multiple reflection on the basis of the signal intensity of the simple reflection, the signal intensity of multiple reflection being a signal intensity of return light generated by being reflected at the plurality of layers three or more times.

(2)

The signal processing apparatus according to (1) above, in which the arithmetic unit is configured to calculate respective signal intensities of the multiple reflection at the third and subsequent layers on the basis of pseudo simple reflection that occurs by decomposing a path of triple reflection occurring at the third and subsequent layers into a path of simple reflection, the surface layer being the first layer among the plurality of layers.

(3)

The signal processing apparatus according to (2) above, in which the arithmetic unit is configured to subtract the respective signal intensities of the multiple reflection at the third and subsequent layers from the signal intensity of the simple reflection including the pseudo simple reflection.

(4)

The signal processing apparatus according to any one of (1) to (3) above, in which the arithmetic unit is configured to calculate signal intensities of the simple reflection of the second and subsequent layers on the basis of reflectances of the second layer and subsequent layers and transmittances of the first layer and subsequent layers among the plurality of layers.

(5)

The signal processing apparatus according to (4) above, in which the arithmetic unit is configured to set an absorptance to be constant in the plurality of layers and calculate the transmittance as a value obtained by subtracting the absorptance and the reflectance from 1.

(6)

An optical tomographic measurement apparatus, including:

an optical system that generates measurement light, reference light, and interference light between the reference light and return light of the measurement light from a measurement object;

a detector that detects the interference light generated by the optical system; and an arithmetic unit configured to calculate a signal intensity of simple reflection among the return light of the measurement light, the simple reflection being one time of reflection at a plurality of layers virtually set in a depth direction from a surface layer side of the measurement object, and calculate a signal intensity of multiple reflection on the basis of the signal intensity of the simple reflection, the signal intensity of multiple reflection being a signal intensity of return light generated by being reflected at the plurality of layers three or more times.

(7)

A signal processing method for generating measurement light and reference light and measuring a tomographic structure of a measurement object on the basis of a signal intensity of interference light between the reference light and return light of the measurement light from the measurement object, the signal processing method including:

calculating a signal intensity of simple reflection among the return light of the measurement light, the simple reflection being one time of reflection at a plurality of layers virtually set in a depth direction from a surface layer side of the measurement object; and calculating a signal intensity of multiple reflection on the basis of the signal intensity of the simple reflection, the signal intensity of multiple reflection being a signal intensity of return light generated by being reflected at the plurality of layers three or more times.

REFERENCE SIGNS LIST 10 light source
21, 22 fiber coupler
30, 130 reference mirror
40 differential detector
50 galvanometer scanner
100 signal processing apparatus
110 broadband light source
120 beam splitter
140 photodetector

The invention claimed is:

1. A signal processing apparatus comprising:
a memory configured to store instructions; and
a Central Processing Unit (CPU) coupled with the memory, wherein the CPU is configured to execute the instructions stored in the memory to:
calculate a signal intensity of simple reflection among return light of measurement light from a measurement object,
wherein the simple reflection is one time of reflection at a plurality of layers, and
wherein the plurality of layers are virtually set in a depth direction from a surface layer side of the measurement object;
calculate a signal intensity of multiple reflection based on the signal intensity of the simple reflection,
wherein the signal intensity of the multiple reflection is a signal intensity of the return light that is reflected at the plurality of layers at least three times; and
control a display screen to display intensity distribution of the signal intensity of the simple reflection and the signal intensity of the multiple reflection.

2. The signal processing apparatus according to claim 1, wherein the plurality of layers includes at least a first layer, a second layer, and a third layer,
wherein the first layer is a surface layer of the measurement object, and
wherein the CPU is further configured to:
decompose a first path of a triple reflection, which is associated with the third layer and a set of layers of the plurality of layers, into a second path of the simple reflection,
wherein the set of layers includes layers of the plurality of layers other than the first layer, the second layer, and the third layer; and
calculate respective signal intensities of the multiple reflection at the third layer and the set of layers based on a pseudo simple reflection that corresponds to the decomposition of the first path of the triple reflection.

3. The signal processing apparatus according to claim 2, wherein the CPU is further configured to subtract the respective signal intensities of the multiple reflection at the third layer and the set of layers from the signal intensity of the simple reflection including the pseudo simple reflection.

4. The signal processing apparatus according to claim 1, wherein the CPU is further configured to:
subtract the signal intensity of the simple reflection of an n-th layer from the signal intensity of the multiple reflection of the n-th layer; and
calculate a value of a reflectance of the n-th layer based on a result of the subtraction and a transmittance of an n−1-th layer, wherein n is a natural number of 2 or more than 2.

5. The signal processing apparatus according to claim 4, wherein the CPU is further configured to:
set, as a constant value, an absorptance in the plurality of layers; and
calculate a value of the transmittance based on subtraction of the constant value of the absorptance and the value of the reflectance from 1.

6. An optical tomographic measurement apparatus, comprising:
an optical system configured to generate measurement light, reference light, and interference light between the reference light and return light of the measurement light from a measurement object;
a detector configured to detect the interference light;
a display screen; and
a Central Processing Unit (CPU) configured to:
calculate a signal intensity of simple reflection among the return light of the measurement light,
wherein the simple reflection is one time of reflection at a plurality of layers, and
wherein the plurality of layers are virtually set in a depth direction from a surface layer side of the measurement object;
calculate a signal intensity of multiple reflection based on the signal intensity of the simple reflection, wherein the signal intensity of the multiple reflection is a signal intensity of the return light that is reflected at the plurality of layers at least three times; and control the display screen to display intensity distribution of the signal intensity of the simple reflection and the signal intensity of the multiple reflection.

7. A signal processing method comprising:

calculating a signal intensity of simple reflection among return light of measurement light from a measurement object, wherein the simple reflection is one time of reflection at a plurality of layers virtually, and wherein the plurality of layers are set in a depth direction from a surface layer side of the measurement object;

calculating a signal intensity of multiple reflection based on the signal intensity of the simple reflection, wherein the signal intensity of the multiple reflection is a signal intensity of the return light that is reflected at the plurality of layers at least three times; and controlling a display screen to display intensity distribution of the signal intensity of the simple reflection and the signal intensity of the multiple reflection.

\* \* \* \* \*